US011155777B2

(12) United States Patent
Mahajan et al.

(10) Patent No.: US 11,155,777 B2
(45) Date of Patent: *Oct. 26, 2021

(54) BIOREACTORS WITH MULTIPLE OR ADJUSTABLE-POSITION AGITATOR DESIGNS

(71) Applicant: Genentech, Inc., South San Francisco, CA (US)

(72) Inventors: Ekta Mahajan, South San Francisco, CA (US); Kelsey Dent, South San Francisco, CA (US); Edward Chan, South San Francisco, CA (US); Terry Hudson, South San Francisco, CA (US); Neria Daniel, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,733

(22) Filed: Dec. 27, 2019

(65) Prior Publication Data
US 2020/0131463 A1  Apr. 30, 2020

Related U.S. Application Data

(60) Division of application No. 15/071,109, filed on Mar. 15, 2016, now Pat. No. 10,563,161, which is a
(Continued)

(51) Int. Cl.
*C12M 3/00* (2006.01)
*C12M 1/00* (2006.01)
(Continued)

(52) U.S. Cl.
CPC .......... *C12M 27/02* (2013.01); *B01F 7/1695* (2013.01); *B01F 13/0872* (2013.01);
(Continued)

(58) Field of Classification Search
CPC .............................. C12M 23/48; C12M 27/02
See application file for complete search history.

(56) References Cited

U.S. PATENT DOCUMENTS

| 4,256,839 A | 3/1981 | Solomons |
| 5,061,079 A | 10/1991 | Shiobara |

(Continued)

FOREIGN PATENT DOCUMENTS

| CN | 101163538 A | 4/2008 |
| CN | 102421511 A | 4/2012 |

(Continued)

OTHER PUBLICATIONS

Extended European Search Report dated Jul. 6, 2017, for EP Application No. 14844125.6, filed on Feb. 25, 2016, 12 pages.
(Continued)

*Primary Examiner* — Nathan A Bowers
(74) *Attorney, Agent, or Firm* — Morrison & Foerster LLP

(57) ABSTRACT

Described herein are bioreactor support structures configured to be used with containers having different designs, and methods for making and using such bioreactors. The support structures described herein may include two or more agitator motors and control systems or an adjustable-position agitator motor, a removable spacer and/or lid, multiple configurations for ports and probes, and multiple exhaust filter heating blankets. Also described herein are methods of manufacturing a multi-agitator motor or adjustable-position agitator motor bioreactor, as well as methods of modifying an existing support structure to be used with a container not originally designed to be used with the existing support structure, and methods for operating these bioreactors.

20 Claims, 13 Drawing Sheets

Related U.S. Application Data continuation of application No. PCT/US2014/055674, filed on Sep. 15, 2014.

(60) Provisional application No. 61/878,516, filed on Sep. 16, 2013.

(51) Int. Cl.
| | | |
|---|---|---|
| *C12M 1/06* | (2006.01) | |
| *B01F 7/16* | (2006.01) | |
| *B01F 15/00* | (2006.01) | |
| *B01F 13/08* | (2006.01) | |
| *C12M 1/02* | (2006.01) | |
| *C12M 1/36* | (2006.01) | |
| *B01F 15/06* | (2006.01) | |

(52) U.S. Cl.
CPC .... *B01F 15/0085* (2013.01); *B01F 15/00538* (2013.01); *B01F 15/00733* (2013.01); *B01F 15/066* (2013.01); *C12M 23/14* (2013.01); *C12M 23/28* (2013.01); *C12M 23/48* (2013.01); *C12M 23/52* (2013.01); *C12M 41/18* (2013.01); *C12M 41/22* (2013.01); *C12M 41/48* (2013.01); *B01F 2015/00597* (2013.01); *B01F 2015/00603* (2013.01); *B01F 2015/062* (2013.01); *B01F 2215/0073* (2013.01)

(56) References Cited

U.S. PATENT DOCUMENTS

| | | |
|---|---|---|
| 6,923,567 B2 | 8/2005 | Bibbo |
| 7,086,778 B2 | 8/2006 | Terentiev |
| 7,267,479 B2 | 9/2007 | Terentiev |
| 7,357,567 B2 | 4/2008 | Terentiev |
| 7,384,027 B2 | 6/2008 | Terentiev |
| 7,481,572 B2 | 1/2009 | Terentiev |
| 7,682,067 B2 | 3/2010 | West |
| 7,695,186 B2 | 4/2010 | Terentiev |
| 7,832,922 B2 | 11/2010 | Schoeb |
| 8,124,403 B2 | 2/2012 | Goodwin |
| 8,187,867 B2 | 5/2012 | Kunas |
| 8,381,780 B2 | 2/2013 | Fisher |
| 8,455,242 B2 | 6/2013 | Staheli |
| 8,505,315 B2 | 8/2013 | Kasza |
| 8,506,198 B2 | 8/2013 | West |
| 8,790,913 B2 | 7/2014 | Zeikus |
| 8,870,443 B2 | 10/2014 | Greller |
| 9,314,751 B2 | 4/2016 | Goodwin |
| 10,563,161 B2 | 2/2020 | Mahajan |
| 2002/0105856 A1 | 8/2002 | Terentiev |
| 2004/0027912 A1 | 2/2004 | Bibbo |
| 2006/0092761 A1 | 5/2006 | Terentiev |
| 2006/0280028 A1 | 12/2006 | West |
| 2007/0253288 A1 | 11/2007 | Mennenga |
| 2009/0130740 A1 | 5/2009 | Ophardt |
| 2009/0142627 A1 | 6/2009 | Schoeb |
| 2009/0176301 A1 | 7/2009 | Oldenburg |
| 2009/0255276 A1 | 10/2009 | Kasza |
| 2010/0255582 A1 | 10/2010 | Porter |
| 2011/0003366 A1 | 1/2011 | Zeikus |
| 2011/0013473 A1 | 1/2011 | Ludwig |
| 2011/0026360 A1 | 2/2011 | Greller |
| 2011/0207218 A1 | 8/2011 | Staheli |
| 2011/0249526 A1 | 10/2011 | Wong |
| 2012/0003733 A1 | 1/2012 | Gueneron |
| 2012/0040449 A1 | 2/2012 | Zambaux |
| 2012/0164720 A1 | 6/2012 | Bierer |
| 2012/0177533 A1 | 7/2012 | Lee |
| 2013/0101982 A1 | 4/2013 | Goodwin |
| 2013/0186834 A1 | 7/2013 | Vicalvi |

FOREIGN PATENT DOCUMENTS

| | | |
|---|---|---|
| EP | 2065085 A1 | 6/2009 |
| GB | 1584103 A | 2/1981 |
| JP | S545091 A | 1/1979 |
| JP | S61104780 | 5/1986 |
| JP | 2007522801 A | 8/2007 |
| JP | 2009539408 A | 11/2009 |
| JP | 2012517217 A | 8/2012 |
| JP | 2012521210 A | 9/2012 |
| RU | 98002 U1 | 9/2010 |
| WO | 2008088371 A2 | 7/2008 |
| WO | 2008088371 A3 | 4/2009 |
| WO | 2013040161 A1 | 3/2013 |

OTHER PUBLICATIONS

International Search Report dated Feb. 20, 2015, for PCT Application No. PCT/US14/55674, filed on Sep. 14, 2014, 4 pages.

Written Opinion dated Feb. 20, 2015, for PCT Application No. PCT/US14/55674, filed on Sep. 14, 2014, 6 pages.

European Examination Report dated Jun. 25, 2021, for EP Application No. 14844125.6, filed Feb. 25, 2016, 10 pages.

BIOREACTORS WITH MULTIPLE OR ADJUSTABLE-POSITION AGITATOR DESIGNS

CROSS-REFERENCE TO RELATED APPLICATIONS

This Application is a divisional of U.S. application Ser. No. 15/071,109, filed Mar. 15, 2016; which is a continuation of PCT Application No. PCT/US2014/055674, filed Sep. 15, 2014; which claims the priority benefit of U.S. Provisional Application No. 61/878,516, filed Sep. 16, 2013; the contents of each of which is incorporated herein by reference in its entirety.

BACKGROUND

Bioreactors may be used for the production of products such as pharmaceuticals, vaccines, antibodies, and the like, through the cultivation of cells, organisms, cultures, and the like under controlled environments. Increasingly, single-use bioreactors are being used, which comprise a support structure and a single-use container configured to fit within the support structure. The use of such systems allows for simpler cleaning and sterilization of the bioreactor between processes. A number of designs for single-use bioreactors exist, and in some situations, a particular design may be desirable—for instance, the use of single-use containers made of particular materials or having a particular agitator system design may be desirable for the production of particular products. The disposable components in a single-use bioreactor are configured for use with a specific bioreactor system, with an arrangement of ports and connectors tailored to that system.

BRIEF SUMMARY

In some cases, it may be costly and/or inefficient to need to use different support structures with different single-use containers. Instead, it may be desirable to be able to use a single support structure with multiple single-use container designs. Described herein are bioreactor support structures configured to be used with containers having different designs, and methods for making and using such bioreactors. The support structures described herein may include two or more agitator motors and control systems or an adjustable-position agitator motor, a removable spacer and/or lid, multiple configurations for ports and probes, and multiple exhaust filter heating blankets. Also described herein are methods of manufacturing a multi-agitator motor and/or adjustable-position agitator motor bioreactor, as well as methods of modifying an existing support structure to be used with a container not originally designed to be used with the existing support structure. Also described herein are methods for operating the bioreactor support structures described here.

A particular embodiment comprises a bioreactor, comprising a support structure configured to hold a container, and an agitator system comprising an impeller and an agitator motor, wherein the agitator system and the support structure are configured to position the agitator motor at a plurality of positions relative to the support structure. The support structure may comprise a top region and a bottom region, and the plurality of positions may comprise a top-mounted agitator motor position and a bottom-mounted agitator motor position. The plurality of positions further comprises at least one intermediate position between the top-mounted agitator motor position and the bottom-mounted agitator motor position. The agitator motor may be mounted on an adjustable-length shaft. The agitator motor may be selectively mountable at the plurality of positions. The support structure may comprise a top region and a bottom region, and the impeller may be configured to be selectively operated at a range of intermediate locations between the top region and bottom region of the support structure. The impeller may be mounted on an adjustable-length shaft. The bioreactor may further comprise a container configured to reside in the support structure and to be coupled to the agitator motor, wherein the container is a collapsible bag. The collapsible bag may be configured for use with a top-mounted agitator motor. The collapsible bag may be configured for use with a bottom-mounted agitator motor. The bioreactor may further comprise a spacer with a raised support surface configured to be removably positioned at the bottom of the support structure. The support structure may comprise a top opening and a removable lid configured to at least partially cover the top opening. The lid may be attached to the support structure when covering the top opening and when removed from the top opening. The support structure may be configured to be used with both internal probes and external probes.

A particular embodiment comprises a support structure comprising a sidewall and a base, forming a cavity therein, the cavity configured to hold a container, a top-mounted agitator motor coupled to the support structure, and a bottom-mounted agitator motor coupled to the support structure, wherein the top- and bottom-agitator motors are configured to be selectively used based on a configuration of the container. The bioreactor may further comprise at least one connector in at least one of the sidewall and base, configured to attach the container. The bioreactor may further comprise a container configured to reside in the cavity and to be coupled to the top- or bottom-mounted agitator motor, wherein the container is a collapsible bag. The bioreactor may further comprise a spacer with a raised support surface configured to be removably positioned at the bottom of the support structure. The spacer may be configured to separate the container and the bottom-mounted agitator motor when the spacer is at the bottom of the support structure. The bioreactor may further comprise a first control system configured to control the top-mounted agitator motor and a second control system configured to control the bottom-mounted agitator motor. The bioreactor may further comprise a selector to switch between the first and second control systems. The first and second control systems may be configured to be selectively employed using a digital user interface. The first and second control systems may comprise variable frequency drives. The support structure may comprise a top opening and a removable lid configured to at least partially cover the top opening. The lid may be attached to the support structure when covering the top opening and when removed from the top opening. The bioreactor may further comprise at least two exhaust filter heating blankets. The at least two exhaust filter heating blankets may have different sizes. The at least two exhaust filter heating blankets may be configured to be selectively employed based on the configuration of the container. The at least two exhaust filter heating blankets may be mounted to a rotatable element, and the at least two exhaust filter heating blankets may be configured to be selectively employed by rotating the rotatable element. The support structure may further comprise one or more probe access ports. At least one of the probe access ports may be configured to accommodate an internal probe. The sidewall may comprise a main body and a door, wherein the one or more probe access ports are located on the door of the sidewall. The sidewall may comprise a main body and a door, and wherein the top-mounted agitator motor is mounted to the door. The sidewall may comprise a main body and a door, and wherein the top-mounted agitator motor is mounted to the main body.

A particular embodiment comprises a method of modifying a bioreactor, comprising attaching a second agitator motor to a support structure comprising a first agitator motor, and adding an access region to the support structure. The first agitator motor may be a bottom-mounted agitator motor, and the second agitator motor may be a top-mounted agitator motor. The first agitator motor may be a top-mounted agitator motor, and the second agitator motor may be a bottom-mounted agitator motor. The support structure may comprise a sidewall main body and a door, and wherein adding an access region may comprise adding an access panel to the door. The support structure may comprise a base, and the method may further comprise providing a fitted removable spacer configured for placement above the base of the support structure. The support structure may comprise a top opening and a lid covering at least portion of the top opening, and adding an access region may comprise modifying the lid to increase internal access to the support structure. The method may further comprise attaching the lid to the support structure using a flexible element that remains attached to the lid when the lid is removed from the top opening of the support structure. Adding an access region may comprise adding one or more probe access ports to the bioreactor. The probe access ports may be configured to accommodate internal probes. The bioreactor may comprise an original exhaust filter heating blanket, and the method may further comprise adding an additional exhaust filter heating blanket to the bioreactor. The additional exhaust filter heating blanket may be a different size than the original exhaust filter heating blanket. The original and additional exhaust filter heating blankets may be configured to be selectively employed. Adding an additional exhaust filter heating blanket to the bioreactor may comprise mounting the additional exhaust filter heating blanket to a rotatable element connected to the support structure. The method may further comprise adding a control system configured to control the second agitator motor. The method may further comprise adding a selector to switch between the original and added control systems. The original and added control systems may be configured to be selectively employed using a digital user interface.

A particular embodiment comprises a method of operating a bioreactor comprising a support structure and a multi-agitator motor system, comprising selecting a bioreactor bag from a group consisting of top-mounted agitator bags and bottom-mounted agitator bags, selecting between a top-mounted agitator motor and a bottom-mounted agitator motor of the support structure, placing the selected bioreactor bag into the support structure; and coupling the selected bioreactor bag to the selected agitator motor. The method may further comprise confirming the presence of a spacer inside the bioreactor. The method may further comprise placing the spacer inside the bioreactor. The method may further comprise removing the spacer from inside the bioreactor. The method may further comprise attaching a bag connector to a support structure connector. The method may further comprise changing a vertical position of the top-mounted agitator motor.

BRIEF DESCRIPTION OF THE DRAWINGS

FIGS. 4A-4B show top perspective and side elevational views of the bioreactor, respectively, having a lid in a first position. FIG. 4C shows a side view of the bioreactor having a lid in a second position.

DETAILED DESCRIPTION

Single-use bioreactors generally comprise a container and a support structure configured to support the container and other items coupled to the container, Typically, the support structure and container are designed to be used together, making the use of an alternative container design with an existing support structure difficult. However, it may at times be desirable to use a single support structure to support containers having different designs. Described herein are bioreactor support structures configured to be used with containers having different designs, and methods for using such bioreactors. Bioreactors are typically classified as either having a top- or bottom-mounted agitator motor, but the support structures described herein may include two or more agitator motors and control systems and/or an adjustable-position agitator motor, a removable spacer and/or lid, multiple configurations for ports and probes, and multiple exhaust filter heating blankets. Also described herein are methods of manufacturing a multi-agitator motor bioreactor and/or adjustable-position agitator motor bioreactor, as well as methods of modifying an existing support structure to be used with a container not originally designed to be used with the existing support structure and methods for using such bioreactors. These methods of modifying an existing support structure may include some or all of modifying an existing support structure to add one or more additional agitator motors or to configure an agitator motor to be adjustable, to add removable spacers, additional configurations for ports and probes, and exhaust filter heating blankets, and/or to remove or modify an existing lid. Also described herein are methods for operating the bioreactor support structures described here, and operating the bioreactor support structures made as a result of the modification methods described here. These bioreactors may be used for production processes with different disposable or single-use container configurations, while still meeting mass transfer coefficient and culture performance standards with each container configuration.

Figure 1A:
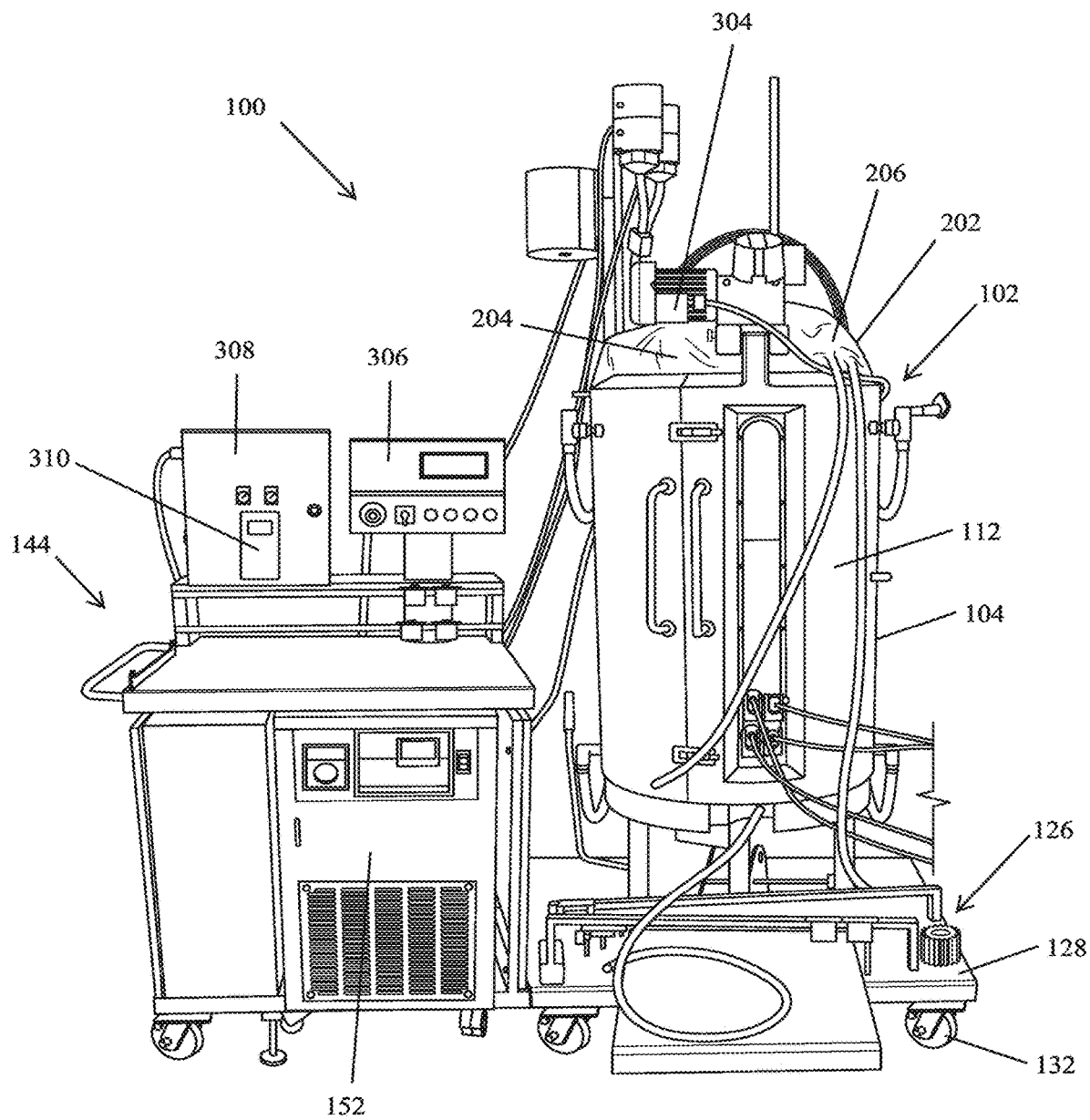
FIG. 1A depicts a side elevational view of an embodiment of a bioreactor described here having top- and bottom- mounted agitator motors.
Figure 1B:
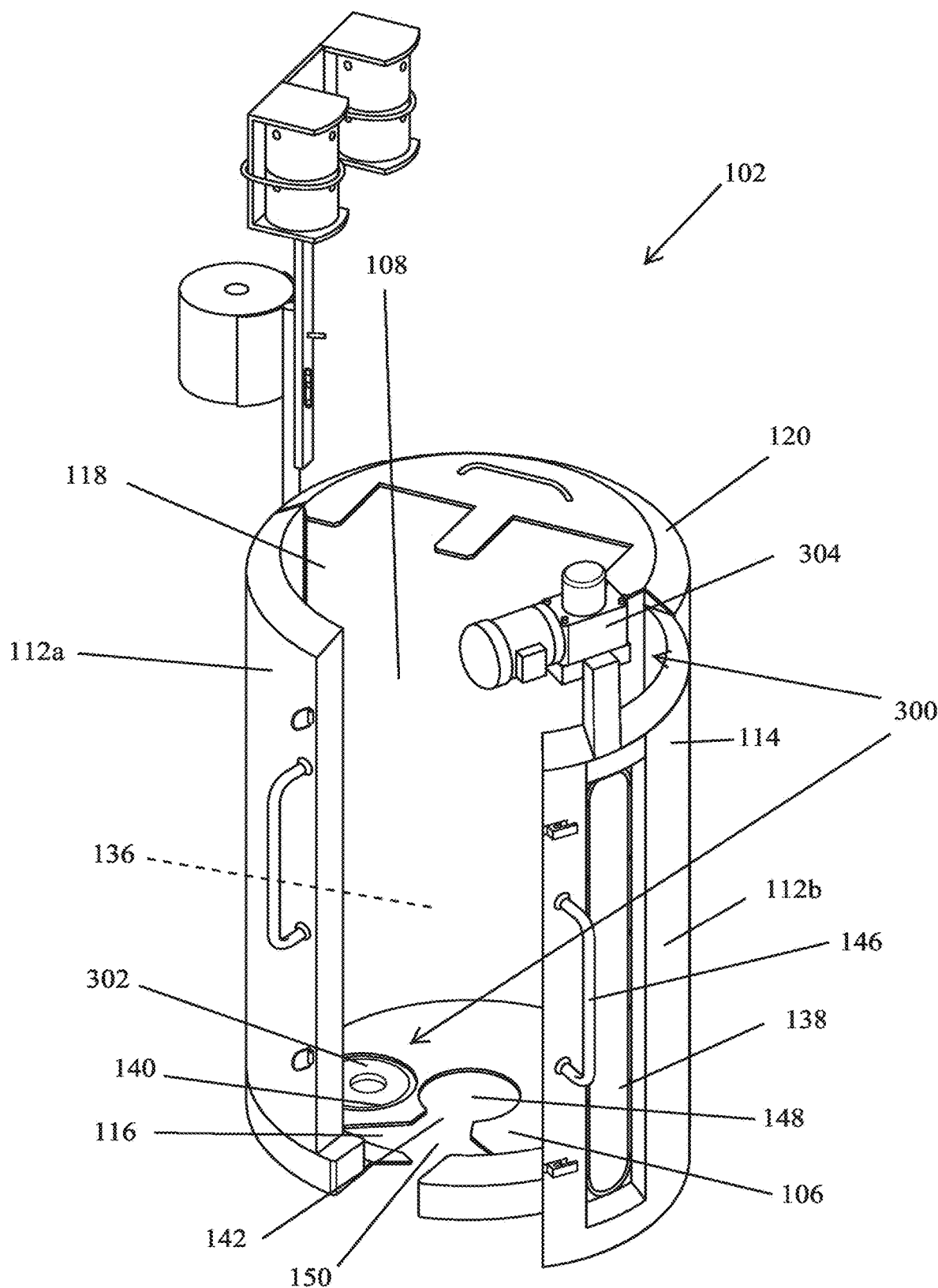
FIGS. 1B-1C depict perspective views of the support structure of bioreactor of FIG. 1A with its doors open and closed, respectively.

FIG. 1A depicts a side elevational view of an embodiment of a bioreactor 100 described here configured for use with containers having different configurations. As shown, bioreactor 100 may comprise a support structure 102 and a container 202. As shown, the support structure 102 may comprise a sidewall 104. While shown in FIGS. 1A-1C as being substantially cylindrical and forming a bottom opening 116 and a top opening 118, the sidewall 104 may comprise any suitable shape configured to support a container, described in more detail below. The sidewall 104 may comprise an inwardly facing lip 120 at the top opening 118. The sidewall 104 may comprise any material or materials suitable for supporting a container, such as metals (e.g., stainless steel, aluminum, etc.), polymers (e.g., high-density polyethylene, polyacrylate, polycarbonate, polystyrene, nylon, or other polyamids, polyesters, phenolic polymers), glass, fiberglass, or the like. The bottom opening 116 of the sidewall 104 may be attached to a base 106 as shown in FIG. 1B, which may partially (or in some variations completely) cover the opening 116. In some variations, the base 106 may be integral to the sidewall 104, in conjunction with the sidewall 104, the base 106 may create a chamber 108, though as shown in FIG. 1B, the chamber 108 may not by fully enclosed at its bottom by base 106. The base 106 may have a concave shape, such as a conical shape, or in other variations, the base 106 may have a flat or convex shape. In the variation shown in FIG. 1B, the base 106 may comprise an opening 140 configured to allow the bottom-mounted agitator motor 302 to interface with the container, as described in more detail below. The opening 140 may be circular as shown, or it may have any suitable shape. The base 106 may additionally or alternatively comprise an opening 142, which may have any suitable shape configured to allow access through the base 106 for elements such as ports, probes, and the sparger, as described in detail below. In the variation of FIG. 1B, the opening 142 may comprise a central region 148 and an outer region 150. The volume of the chamber 108 may be any desired volume, such as but not limited to about 1 L, 3 L, 10 L, 20 L, 40 L, 60 L, 100 L, 150 L, 200 L, 400 L, 600 L, 1,000 L, 2,000 L, 4,000 L, or larger.

Figure 1C:
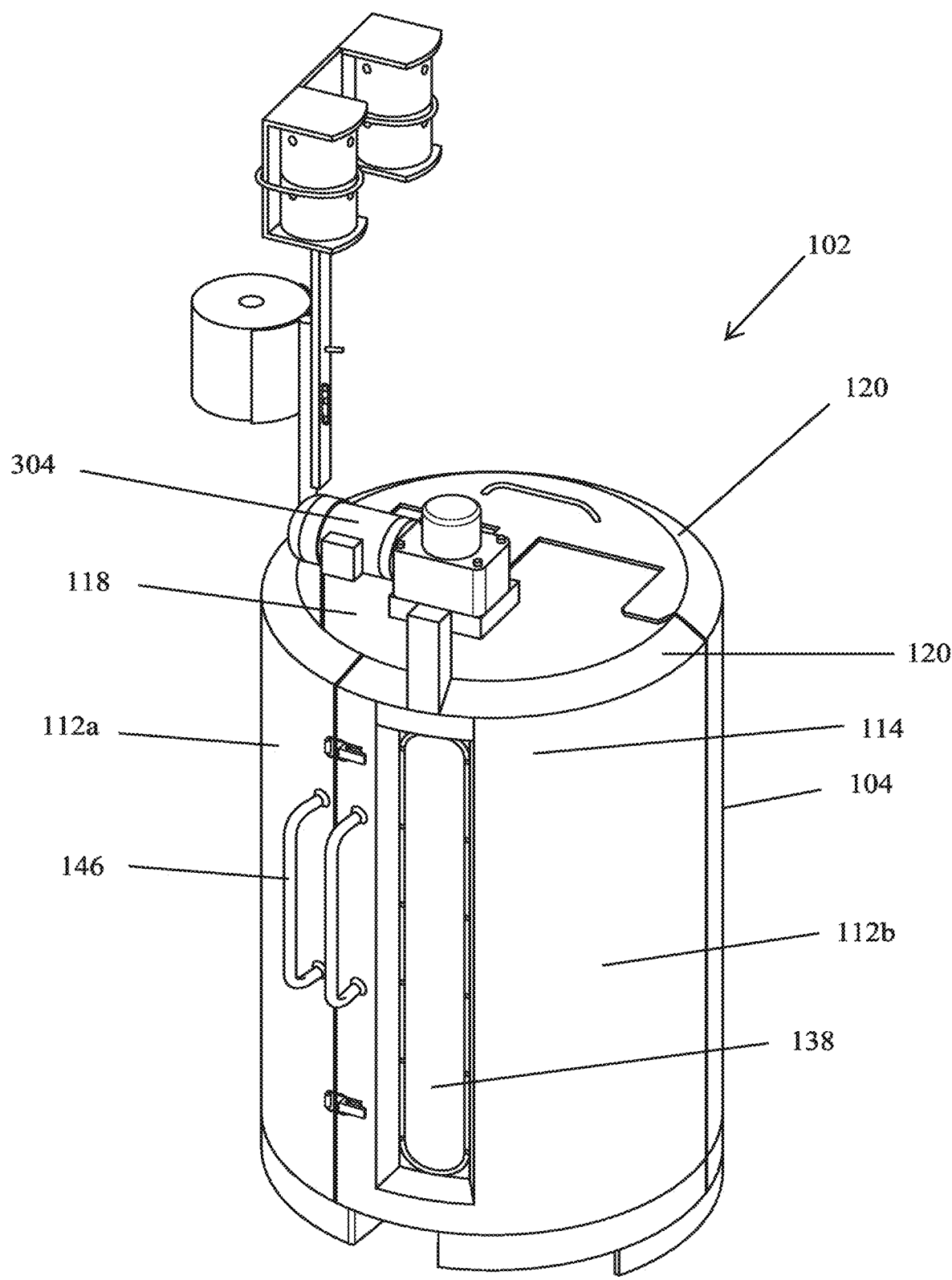

In some variations, a portion of the sidewall 104 may comprise one or more doors 112. As shown in FIGS. 1A-1C, the doors 112 may comprise a radial segment of the sidewall 104. The doors 112 may be attached to the remainder of the sidewall 104 via hinges. In variations having two adjacent doors 112a and 112b, the hinges may be located on opposite sides of the doors 112a and 112b, such that the two doors 112 open outward and away from each other. The doors 112 may comprise handles 146. When the doors 112 are open, this may create an opening in sidewall 104 which may allow for easier placement of a container within the support structure 102. While the doors 112 are shown in FIGS. 1A-1C as extending the full vertical length of the sidewall 104, it should be appreciated that in other variations, the door(s) 112 may extend for only part of the vertical length of the sidewall 104. For instance, the door(s) 112 may extend from the top of sidewall 104 partially down the vertical length of the sidewall 104, or in other variations, the door(s) 112 may extend from an intermediate position along the length of the sidewall 104 to the bottom of the sidewall 104. The doors 112 may optionally comprise transparent or translucent windows 138. It should also be appreciated that although the sidewall 104 is shown in FIGS. 1A-1C as having a first door 112a and a second door 112b, in other variations, the sidewall 104 may comprise only one door, or in yet other variations, the sidewall 104 may comprise no doors.

In some variations, the support structure 102 may comprise a temperature regulation system for regulating the temperature during the bioreactor process. The temperature regulation system may comprise a jacket 136, which may allow for both heating and cooling. The jacket 136 may be located within sidewall 104, between an inner wall and an outer wall of the sidewall 104. In other variations, the jacket may be located within the chamber 108, on the inside of sidewall 104. In some variations, the temperature regulation system may comprise electrical heating elements and/or circulating fluid systems. In variations in which the temperature regulation system comprises circulating fluid systems, there may be one or more fluid channels located in the jacket 136. The fluid channels may have one or more inlets and outlets that allow a fluid (e.g., propylene glycol, water, or the like), which may be heated or cooled by a temperature control unit, to be circulated through the channels to regulate the temperature of the bioreactor.

In some variations, bioreactor 100 may optionally comprise additional elements, as shown in FIG. 1A. For example, the support structure 102 may optionally rest on a support assembly 126, which may raise the height of the support structure 102 off the ground, and/or may allow the support structure 102 to be more easily moved. For example, the support structure 102 may rest on cart 128, which may have attached casters or wheels 132. In other variations, the support structure 102 may rest on the floor or on another surface. The bioreactor 100 may additionally or alternative comprise one or more control carts, which may hold elements used during the production process, such as but not limited to temperature control units, pumps and mass flow controls, media and buffer bags, and controllers, described in more detail below. For example, in the variation shown in FIG. 1A, control cart 144 may hold temperature control units 152 and controllers 306 and 308, described in more detail below, while a second cart (not shown) may hold the mass flow controllers, also described in more detail below. It should be appreciated that in other variations having these elements, they may be held in different configurations on two or more carts, or they may be held by a single cart.

The support structure 102 may be configured to support, surround, and/or contain a container 202, which may be configured to be placed within the chamber 108 of the support structure 102. The container 202 may define a reservoir 204 to hold contents for carrying out the process within the bioreactor 100, such as but not limited to media, reactants, gasses, and other components. In some variations, the container 202 may be configured to be substantially sealed from the outside environment, except through designated points, such as ports and probe connectors (described below). In this way, the container 202 may keep the contents contained and not in contact with all or a portion of the support structure 102. This may allow the support structure 102 to be reused in multiple processes (e.g., by removing the container 202 from the support structure 102 and replacing it with a new container) without requiring the same level of sterilization that would be required without a container 202, while the container 202 may be designed to be single-use or disposable.

In some variations, the container 202 may comprise a bag 206. The bag 206 may be at least partially collapsible and/or at least partially comprise a flexible material, which may be suitable for contact with the contents of the reservoir 204 during the process carried out in the bioreactor 100, and which may be water impermeable. In some variations, the bag 206 may comprise one or more materials, such as but not limited to polycarbonate, polyethylene, polypropylene, polyvinylchloride, polyvinyldichloride, polyvinylidene chloride, ethylene vinyl acetate, polycarbonate, polymethacrylate, polyvinyl alcohol, nylon, and/or synthetic rubbers or plastics, or the like. The bag 206 may have any suitable thickness, such as but not limited to less than about 1 mm, about 1 to 3 mm, or about 3 to 5 mm, or thicker. In some variations, the bag 206 may be single-ply, while in other variations it may be multi-ply. In variations having more than one later, each layer may have the same or a different polymer orientation relative to other adjacent layers. The bag 206 may form the reservoir 204 in any number of ways; for example, in some variations, the hag may comprise two sheets of material that are joined at their edges to create the reservoir 204. In other variations, a single sheet of material may be joined at its edges to create the reservoir 204. In yet other variations, more than two sheets of material may be joined at their edges to create the reservoir 204, such as a single sheet forming a cylindrical portion and two sheets forming top and bottom panels. In some variations, a portion of the container may comprise a rigid material, such as a rigid base. In some variations, the bag 206 may be pre-sterilized and sealed. The bag 206 may further comprise one or more connectors for attaching the bag 206 to the support structure 102, as well as one or more inlet and/or outlet ports, and one or more probe connectors, as described in more detail below.

The reservoir 204 of the hag 206 may have any desired volume, such as but not limited to up to 1 L, 3 L, 10 L, 20 L, 40 L, 60 L, 100 L, 150 L, 200 L, 400 L, 600 L, 1,000 L, 2,000 L, 4,000 L, or greater. It should be appreciated that while single-use bioreactor support structures are generally used with containers having approximately the same dimensions and volume, such correspondence is not necessary, and indeed, support structure 102 may be configured such that the support structure 102 may be used with a bag 206 having a different volume or dimensions as the chamber 108 of support structure 102. For instance, in one variation, the chamber 108 of support structure 102 may have a volume of about 200 L, while it may be used with a bag having a volume of about 250 L. In another variation, the chamber 108 may have a volume of about 200 to 250 L, while it may be used with a bag having volume of about 100 L. In some variations, the chamber 108 of support structure 102 may have a maximum diameter (or maximum distance transverse to the longitudinal axis) of about 20 to 22 inches, while it may be used with a bag having a diameter (or maximum distance transverse to the longitudinal axis) of about 23 to 25 inches, or it may be used with a bag having a diameter (or maximum distance transverse to the longitudinal axis) of about 16 to 18 inches. It should be appreciated that support structures having chambers having a range of volumes and dimensions may be used with bags having a range of volumes and dimensions, not limited to those examples provided here. It should also be appreciated that in some instances in which the temperature regulation system of the support structure 102 comprises a jacket 136 located on the inside of sidewall 104 or within the sidewall 104 between inner and outer walls, if the diameter (or maximum distance transverse to the longitudinal axis) of the bag 206 is smaller than the diameter (or maximum distance transverse to the longitudinal axis) of the support structure 102 to an extent that affects the performance of the temperature regulation system, a component to transfer heat between the jacket 136 and the bag 206 may be added, such as a spacer or other structure to assist with temperature regulation.

Generally, single-use bioreactors comprise an agitator system, which may facilitate mixing of the contents of the container. The agitator may comprise an impeller and an agitator motor configured to rotate the impeller. The impeller may comprise vanes or blades to engage the contents of the container when rotated. The impeller may generally be located within the container, while the agitator motor is located outside of the container, with the coupling between the agitator motor and the impeller configured such that the sterility of the environment within the container may be maintained. In some bioreactors the coupling may be, for example, magnetic, while in others it may be mechanical. Single-use bioreactors generally comprise support structures that have either top-mounted agitator motors or bottom-mounted agitator motors, which are configured to be used with top-mounted agitator containers (that is, containers having impellers configured to be rotated by top-mounted agitator motors) or bottom-mounted agitator containers (that is, containers having impellers configured to be rotated by bottom-mounted agitator motors), respectively. However, as described above, it is desirable that a single support structure be able to be used with containers having different designs, including both top-mounted or bottom-mounted agitator containers.

As such, in one variation, the bioreactor 100 described herein may comprise an agitator system 300 comprising both a bottom-mounted agitator motor and a top-mounted agitator motor. Thus, the bioreactor 100 may be configured to be used with containers having different designs, including those configured for use with both bottom- and top-mounted agitator motors. As shown in FIG. 1B, the bioreactor 100 may comprise a bottom-mounted agitator motor 302. The bottom-mounted agitator motor 302 may be located below base 106 of support structure 102. The base 106 may comprise an opening 140 configured to allow the bottom-mounted agitator motor 302 to interface with the container, as described in more detail below. The opening 140 may be circular as shown, or it may be any suitable shape.

As shown in FIGS. 1A-1C, the bioreactor 100 may additionally comprise a top-mounted agitator motor 304. The top-mounted agitator motor 304 may be mounted to the support structure 102. In the variation shown in FIGS. 1A-1C, the top-mounted agitator motor 304 may be mounted to the top 114 of a door 112 of the sidewall 104. In other variations, the top-mounted agitator motor 304 may be mounted to the lip 120 of the sidewall 104. For example, it may in some instances be desirable to mount the top-mounted agitator motor 304 to a fixed component of the support structure 102. In some instances, it may be desirable to mount the top-mounted agitator motor 304 to a portion of the sidewall 104 above the jacket 136, such that the top-mounted agitator motor 304 does not interfere with the jacket 136. However, in other variations, the top-mounted agitator motor 304 may be mounted to a portion of the sidewall 104 containing the jacket 136. In yet other variations, the top-mounted agitator motor 304 may be mounted to a structure that is separate from the sidewall 104. For instance, the top-mounted agitator motor 304 may be mounted to a rod, which in turn may be attached to cart 144. Alternatively, the top-mounted agitator motor 304 may be mounted to a stand-alone support structure. The top-mounted agitator motor 304 may be mounted via any suitable method, such as by welding the top-mounted agitator motor 304 in place or attaching it via a mounting bracket to the support structure 102.

While the agitator motor 304 is shown as having a fixed position in FIGS. 1A-1C, in other variations, the top-mounted agitator motor 304 may have an adjustable position. In some of these variations, the top-mounted agitator motor may be moved relative to the sidewall 104 of the support structure 102. For example, the top-mounted agitator motor may be slidable along a rail or track. In such a case, the rail or track may allow the top-mounted agitator to be secured at one or more discrete locations along the rail or track. For example, the rail or track may comprise openings for pins, which may allow the top-mounted agitator motor to be secured at various locations along the rail or track, corresponding to various vertical, horizontal, or radial positions relative to the sidewall of the support structure. In other variations, the rail or track may allow the top-mounted agitator to be secured at any location along the rail or track. As another example, the top-mounted agitator motor may be removably secured to one of a plurality of mounting brackets located at various positions relative to the sidewall of the support structure. The top-mounted agitator motor may then be selectively secured to one of the mounting brackets (using, for example, a removable pin) at the desired position. By having an adjustable position, the top-mounted agitator motor may, for example, be able to be positioned and operated at a range of intermediate locations between the top and bottom regions of the support structure 102. A vertically-moveable top-mounted agitator motor may have advantages such as providing additional flexibility in allowing use of containers having a shorter height than the chamber of the support structure to be agitated by the top-mounted agitator motor, or allowing a container to have a lower minimum working volume. Moreover, an adjustable-position agitator motor may allow the position of the agitator to be moved during a process run, for instance, as the working volume is increased.

In other variations, in order for a single support structure be able to be used containers with different designs, the bioreactors described here may comprise only a single agitator motor that has an adjustable position. Like the multi-agitator motor design having an adjustable-position top-mounted agitator motor, in a single-agitator motor design having an adjustable-position agitator motor, the single agitator motor may be moved vertically, horizontally, and/or radially relative to the support structure, and/or may be rotated relative to the support structure. By having an adjustable position, the agitator motor may be able to be positioned and operated at a range of locations. In some variations, these positions may include a top-mounted agitator position and a bottom-mounted agitator position (that is, positions allowing the agitator motor to be used with containers configured for use with top- and bottom-mounted agitators, respectively). In other variations, these positions may optionally additionally include one or more intermediate locations between the top and bottom positions. An adjustable-position agitator motor may have advantages such as but not limited to providing additional flexibility in allowing use of the motor to operate the impeller of either a top-mounted or bottom-mounted agitator container, allowing use of the motor to rotate the impeller of a top-mounted agitator container having a shorter height than chamber of the support structure, or allowing a container to have a lower minimum working volume. Moreover, an adjustable-position agitator motor may allow the position of the agitator to be moved during a process run.

In one example of an adjustable-position agitator motor, the agitator motor may be slidable along a rail or track, in a manner similar to that described above with respect to a top-mounted agitator motor. In some variations the track may run along the perimeter of the support structure to allow the agitator motor to be horizontally adjustable around the circumference of the support structure. In other variations the rail or track may run vertically to allow the agitator motor to be vertically adjustable up and down relative to the support structure. In other variations, the track may be configured such that the agitator motor may be radially adjustable toward and away from the center of the support structure. In yet other variations, the angle of the agitator motor may be adjusted. In some variations, the track may be configured such that the agitator motor may be adjustable along two or more of these dimensions. The rail or track and agitator motor may configured such that the agitator motor may be selectively secured at discrete locations along the rail or track, or they may be configured such that the agitator motor may be selectively secured at any point along the rail or track. The agitator motor may be secured using a mechanism such as but not limited to removable pins, a rack and pinion arrangement, a clamp, or the like. For example, if the agitator motor is secured to the rail or track using pins, the rail or track may comprise a series of openings configured to receive a pin. The agitator motor may be slidably attached to the rail or track via a mount, and may be pushed or pulled along the rail or track until one or more openings in the mount align with one or more openings in the rail or track. One or more pins may then be, inserted into the one or more openings to secure the agitator motor at the desired position. As another example, if the agitator motor is secured to the rail or track using a clamp, the agitator motor may be slidable along the rail or track when the clamp is in a released configuration. In some variations, the agitator motor may be pushed or pulled along the rail or track until the desired position, at which point the clamp may be placed in a tightened configuration to hold the agitator motor in place. In other variations, the agitator motor may be removable from the rail or track when the clamp is in a released configuration. The agitator motor may be placed at the desired position along the rail or track and secured by placing the clamp in a tightened configuration. In some variations, the clamp and rail or track may be configured such that the agitator motor may be clamped at two or more angles relative to the rail or track, allowing the agitator motor to be secured at two or more angles relative to the support structure. In variations in which the agitator motor is pushed or pulled along the rail or track, the agitator motor may be directly pushed or pulled by the user, or it may be indirectly pushed or pulled, such as via a manual mechanism (e.g., a hand crank) or via an automated mechanism (e.g. a motor and user interface or switch). In some variations the rail or track may be secured to the support structure of the bioreactor, while in other variations, the rail or track may be additionally or alternatively secured to a separate structure. For example, the rail or track may be attached to a cart holding other elements used during the bioreactor process (like cart 144 of FIG. 1A), or may be secured to or be part of a stand-alone support structure.

As another example, the agitator motor may have an adjustable position by being secured to a shaft that is in turn adjustable relative to the support structure. That is, the agitator motor may be fixedly attached to a shaft, which is in turn adjustably attached to the support structure. As in the variations described above, the shaft may be adjustable relative to the support structure such that the agitator motor may be moved horizontally, vertically, and/or radially relative to the support structure, and/or such that the angle of the agitator motor relative to the support structure may be adjusted. The shaft may be adjustable relative to the support structure using any suitable mechanism, such as but not limited to being secured via removable pins, a rack and pinion arrangement, a clamp, or the like, to the support structure. For example, the shaft may be adjusted relative to the support structure using removable pins or a clamp in a similar manner as described above with respect to an agitator motor movable along a rail or track. In other variations, the shaft may be attached to a structure that is separate from the support structure of the bioreactor, and the shaft may be adjustable relative to the separate structure, or the separate structure may be adjustable relative to the support structure of the bioreactor. As yet another example, the agitator motor may have an adjustable position by being secured to a shaft that has an adjustable length. In some variations, the shaft may have telescoping segments that may allow for length adjustment. Additionally or alternatively, the shaft may have segments that may be added or removed in order to allow for length adjustment. As above, the shaft may be mounted to the support structure of the bioreactor, or it may be mounted to a separate structure, such as a cart holding other elements used in the bioreactor process (like cart 144 of FIG. 1A) or a stand-alone structure.

Figure 7A:
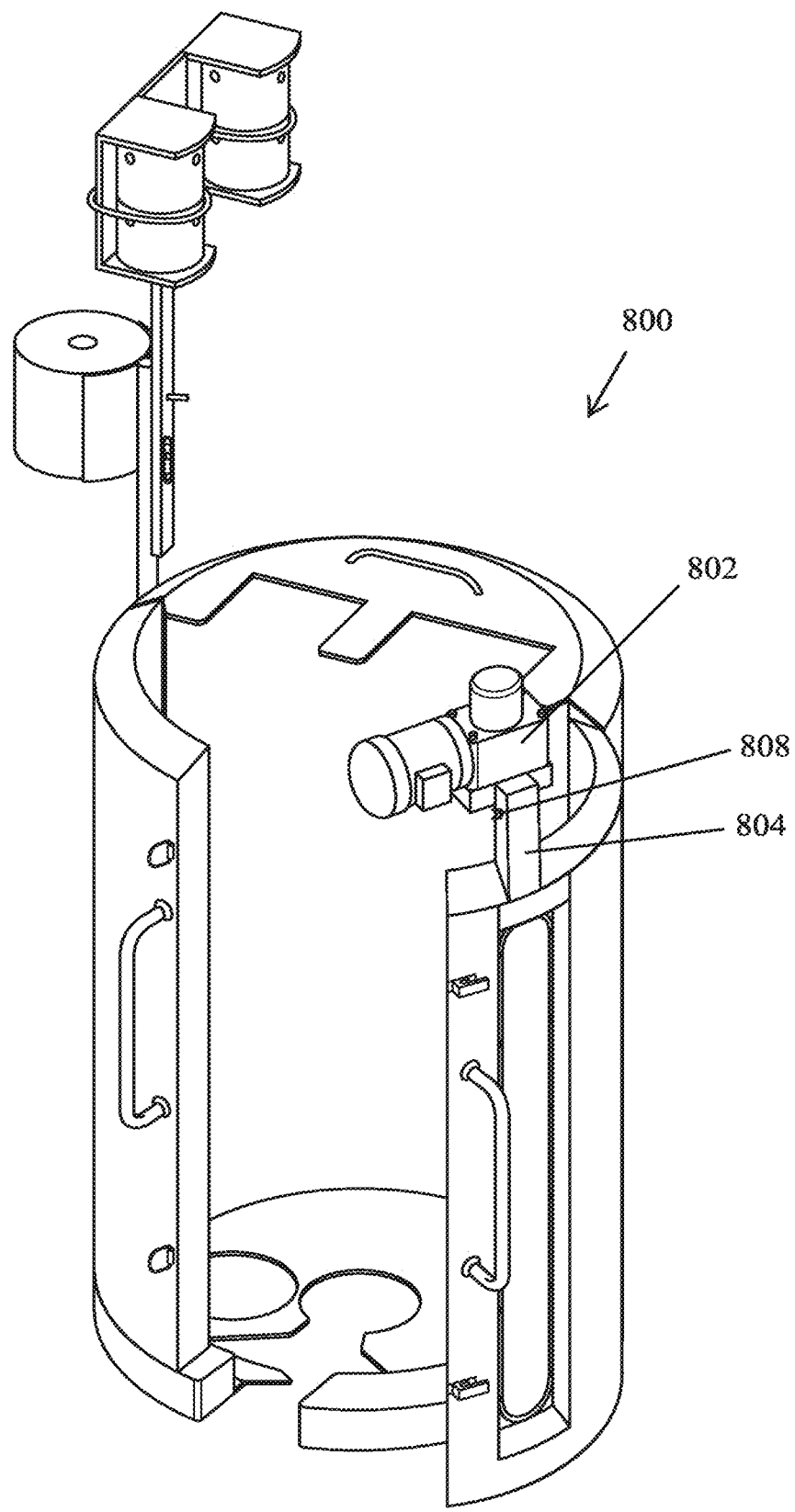
FIGS. 7A-7B depict perspective views an embodiment of a bioreactor described here having an adjustable-position agitator motor, shown in a first position in FIG. 7A and a second position in FIG. 7B.
Figure 7B:
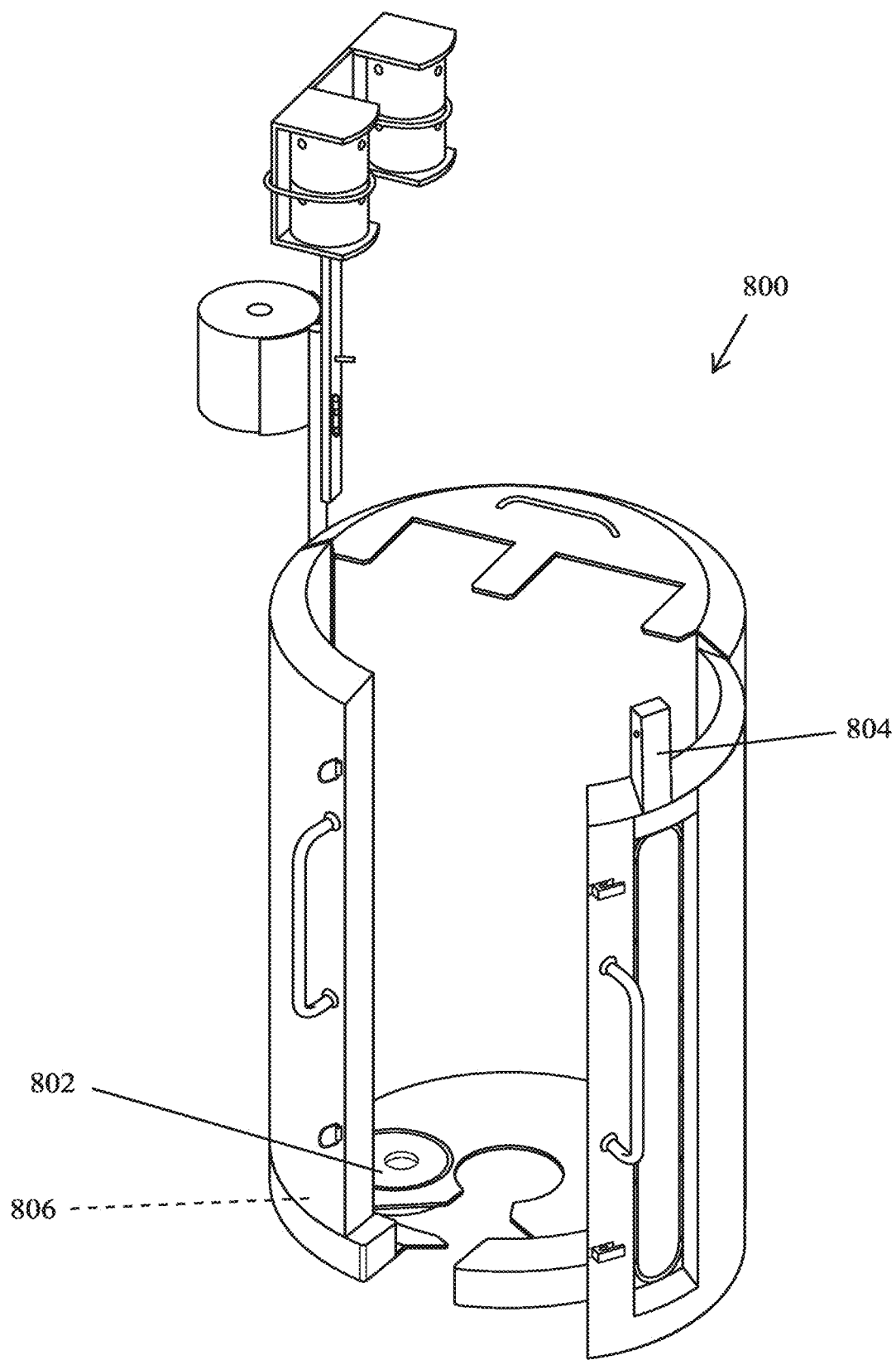

As yet another example, the agitator motor may have an adjustable position by being removably secured to one of a plurality of mounting brackets located at various positions relative to the sidewall of the support structure. The agitator motor may be selectively secured to one of the mounting brackets (using, for example, a removable pin) at the desired position. In some variations, one or more of the mounting brackets may have multiple configurations in which the agitator motor may be attached (e.g., the agitator motor may be secured at a range of angles, and/or at one of multiple locations on the mounting bracket). An example of a bioreactor wherein the agitator motor may be removably secured to one of a plurality of mounting brackets is shown in FIGS. 7A-7B. In bioreactor 800 shown there, the adjustable-position agitator motor 802 may be removably secured to a first mounting bracket 804 or to a second mounting bracket 806. When the adjustable-position agitator motor 802 is removably secured to the first mounting bracket 804, as shown in FIG. 7A, it may be located at a position allowing the agitator motor 802 to be used with a container configured for use with a top-mounted agitator motor. The agitator motor 802 may be secured to the first mounting bracket 804 via pin 808. When the adjustable-position agitator motor 802 is removably secured to the second mounting bracket 806, as shown in FIG. 7B, it may be located at a position allowing the agitator motor 802 to be used with a container configured for use with a bottom-mounted agitator motor. It should be appreciated that the orientation of the agitator motor 802 may be additionally or alternatively adjusted; for example, the attachment site for the container may be facing substantially downward when the agitator motor is secured to the first mounting bracket 804, while the attachment site for the container may be facing substantially upward when the agitator motor is secured to the second mounting bracket 806. Although the mounting brackets to which the agitator motor may be selectively secured in FIGS. 7A-7B are attached to the support structure of the bioreactor 800, it should be appreciated that in other variations, the mounting brackets may be located on a separate structure or cart.

Returning to FIG. 1A, in some variations, the bioreactor 100 may comprise a first control system 306 configured to control the bottom-mounted agitator motor 302, and a second control system 308 configured to control the top-mounted agitator motor 304. In some variations, the first control system 306 and/or second control system 308 may comprise variable-frequency drives. The first control system 306 and second control system 308 may be selectively employed to operate the bottom-mounted agitator motor 302 and top-mounted agitator motor 304, respectively. In some variations, the bioreactor 100 may comprise one or more manual control switches that may be used to selectively turn on and off the first control system 306 and/or the second control system 308, and/or a selector 310 to switch between using the first control system 306 and the second control system 308. In other variations, the bioreactor 100 may additionally or alternatively comprise a user interface that may be used to selectively turn on and off the first control system 306 and/or the second control system 308. In some variations, the user interface may be digital. In some variations, one of the first control system 306 and second control system 308 may be operated at a time, while in other variations, both of the first control system 306 and second control system 308 may be operated at a time. The first control system 306 and second control system 308 may also control, in addition to or instead of whether the bottom-mounted agitator motor 302 and top-mounted agitator motor 304, respectively, are on or off, the rotation speed of the motors. Furthermore, in some variations, the first control system 306 and/or second control system 308 may also control the temperature of heating blankets for the exhaust filters to prevent clogging of the filters, and/or other sensors.

Figure 2A:
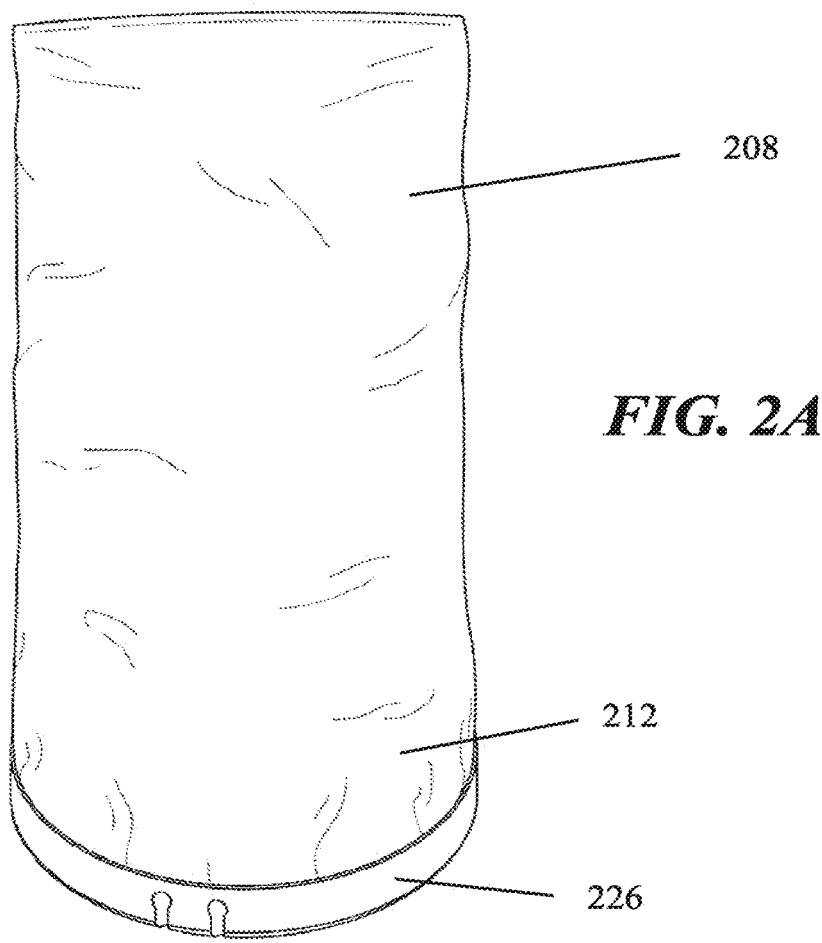
FIG. 2A depicts a perspective view of a bag configured for use with a bottom-mounted agitator motor.
Figure 2B:
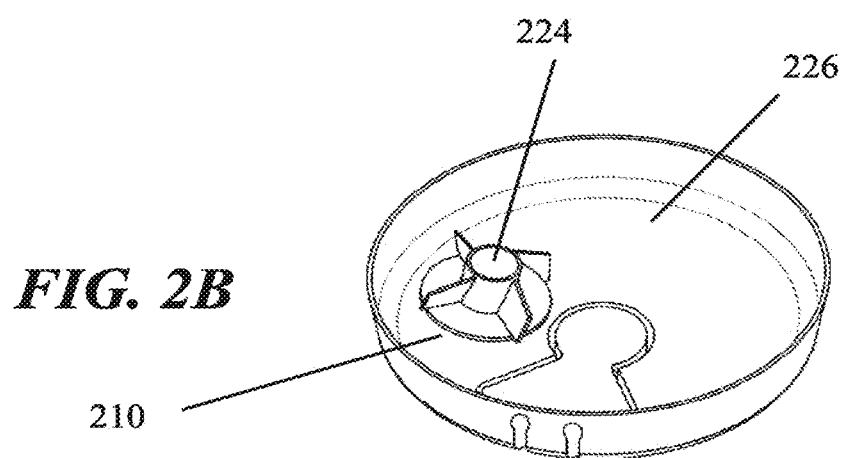
FIG. 2B depicts a perspective view of a rigid base of the bag of FIG. 2A.

In variations comprising both a bottom-mounted agitator motor 302 and a top-mounted agitator motor 304, which in some variations may be selectively employed with separate control systems, the bioreactor 100 may be able to be used with a container configured for use with either a bottom- or top-mounted agitator motor. Similarly, the bioreactor 800 described above having one adjustable-position agitator motor may be able to be used with a container configured for use with either a bottom- or top-mounted agitator motor as well. For example, the bioreactors described herein may be able to be used with a bag 208 configured to be used with a bottom-mounted agitator motor, an example of which is shown in FIGS. 2A-2B. The bag 208 may comprise an agitator port 210 located in a lower portion 212 of the bag 208 configured to interface with a bottom-mounted agitator motor or an adjustable agitator motor in a bottom-mounted position. In some variations, the agitator port 210 may be located in a rigid base 226 attached to the lower portion 212 of the bag 208, which may comprise a rigid or semi-rigid material such as but not limited to low-density or high-density polyethylene, as shown in FIG. 2B. In other variations, the agitator port 210 may be located on a flexible portion of the bag 208. In some variations, the location of the interface, and thus the agitator port 210, may be offset from the center of the support structure 102 and/or bag 208. For example, the interface may be located about 10-20 degrees from the center, about 20-30 degrees from the center, or about 30-40 degrees from the center, or more. The agitator port 210 may be configured to engage with a bottom-mounted agitator motor or an adjustable agitator motor in a bottom-mounted position. In some variations, the base 106 of the support structure 102 may optionally comprise a protrusion to help hold the agitator port 210 in place. The agitator port 210 may allow the bottom-mounted agitator motor 302 to rotate an impeller 224. The bottom-mounted agitator motor 302 may be configured to rotate the impeller 224 at any suitable speed or range of speeds, such as but not limited to about zero to 120 revolutions per minute, about zero to 150 revolutions per minute, or about zero to 360 revolutions per minute. The impeller 224 may have any suitable design. In some variations, the impeller 224 may comprise two, three, four, or more blades, which may have pitch angles of less than 10 degrees, about 10 to 20 degrees, about 20 to 30 degrees, about 30 to 40 degrees, about 40 to 50 degrees, or more. The impeller 224 may have any suitable diameter (or maximum distance transverse to its longitudinal axis), such as less than 5 cm, 5 to 10 cm, 10 to 15 cm, or larger. Although the impeller 224 is shown in FIG. 2B as being in close proximity to the agitator port 210, it should be appreciated that in other variations the vertical position of the impeller 224 may be adjustable relative to the bag 208. For example, the impeller may interface with the agitator port via an agitator shaft having an adjustable length, the impeller may be adjustable along an agitator shaft, or the agitator shaft may be moveable relative to the agitator port.

Figure 2C:
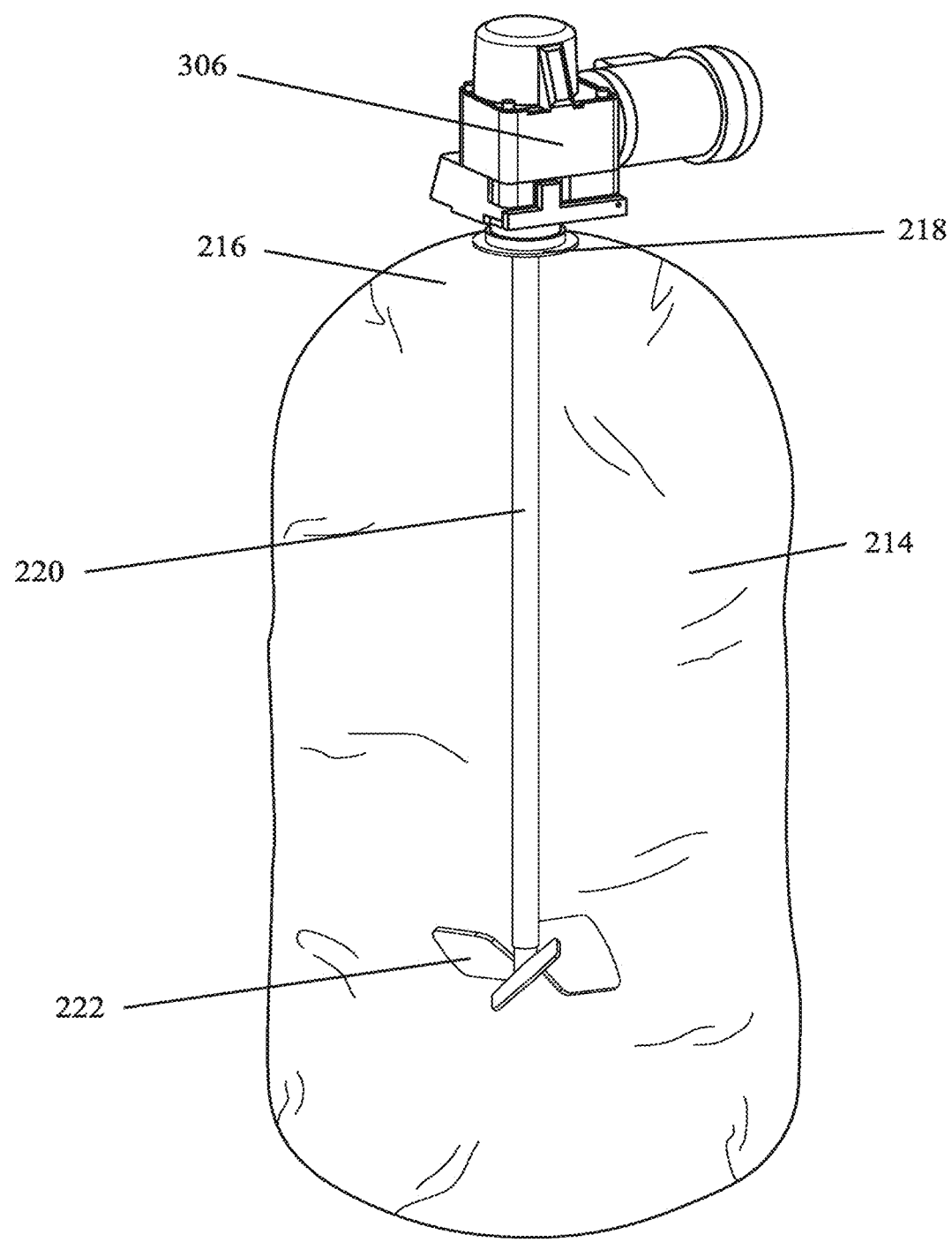
FIG. 2C depicts a perspective view of a hag configured for use with a top-mounted agitator motor.

The bioreactors described herein may also be able to be used with a bag 214 configured to be used with a top-mounted agitator motor or an adjustable agitator motor in a top-mounted position, shown in FIG. 2C. The bag 214 may comprise an agitator port 218 located in a top portion 216 of the bag 214. Within the bag 214, an agitator shaft 220 may be attached to the agitator port 218, and the agitator shaft 220 may in turn be attached to an impeller 222. The agitator motor may be configured to rotate the impeller 222 via the agitator shaft 220 at any suitable speed or range of speeds, such as but not limited to about zero to 120 revolutions per minute, about zero to 150 revolutions per minute, or about zero to 360 revolutions per minute. The impeller 222 may have any suitable design. In some variations, the impeller 222 may comprise two, three, four, or more blades, which may have pitch angles of less than 10 degrees, about 10 to 20 degrees, about 20 to 30 degrees, about 30 to 40 degrees, about 40 to 50 degrees, or more. The impeller 222 may have any suitable diameter maximum distance transverse to its longitudinal axis), such as less than 5 cm, 5 to 10 cm, 10 to 15 cm, or larger.

In some variations, the vertical position of the impeller 222 may be adjustable relative to the bag 214. In these variations, the agitator shaft 220 may have an adjustable length, and/or the position of the impeller 222 may be moveable relative to the agitator shaft 220. For example, the impeller 222 may be fixed to the agitator shaft 220, while the agitator shaft 220 may have one or more portions such that the agitator shaft 220 can be adjusted in length. In some variations, the agitator shaft 220 may have telescoping segments that may allow for length adjustment. Additionally or alternatively, the agitator shaft 220 may have segments that may be added or removed in order to allow for length adjustment. By adjusting the length of the agitator shaft 220 between the location at which the impeller 222 is attached and the agitator port 218, the vertical position of the impeller 222 may be adjusted before or during the process. As another example, the vertical position of the impeller 222 may be adjustable relative to the bag 214 by being configured to be attached to the agitator shaft 220 via one or more removable screws or pins, which may secure the impeller 222 to various vertical positions along the agitator shaft 220. In one such example, the impeller 222 may be mounted to a horizontal plate, which may in turn be configured to the attached to the agitator shaft 220 via one or more removable screws or pins. This may allow the impeller 222 to be moved to the desired vertical position within the container and relative to the agitator shaft 220 before or during the process. As another example, the vertical position of the impeller 222 may be adjustable relative to the bag 214 by the support structure comprising a movable bottom plate that allows the bottom of the bag to be moved vertically relative to the impeller position. If the bottom plate is moved vertically upward relative to the support structure, it may push the bottom up the bag upward (which may cause the bag to fold or compress), thus moving the bottom of the hag toward the impeller. This may effectively decrease the volume of the bag. In some variations, the bottom plate may comprise the spacer 400 described in more detail below, wherein the spacer is configured to be coupled to the inside of the sidewall of the support structure at variable vertical positions (e.g., by tabs or hooks). Having the vertical position of the impeller 222 adjustable relative to the bag 214 in one of the ways described above, or in another manner, may have certain advantages, such as but not limited to allowing the bag 214 to have a lower minimum working volume. Moreover, a vertically adjustable impeller 222 may allow the position of the impeller 222 to be moved during a process run, for instance, as the working volume is increased.

The container (e.g., bag 208 or bag 214) and/or the support structure may comprise one or more connectors for attaching the container to the support structure of the bioreactor (e.g. bioreactor 100 or bioreactor 800), and/or for holding the container in a particular configuration (e.g., pulled into an expanded configuration). In some variations, there may be at least one connector located on either the sidewall or the base of the support structure to attach to the container. For example, the container may comprise a hag connector (e.g., a hook) configured to be attached to a support structure connector. In other variations, the container and the support structure may not comprise connectors, and instead, the container may be held in place via attachment to the agitator motor, described in more detail above.

Figure 3A:
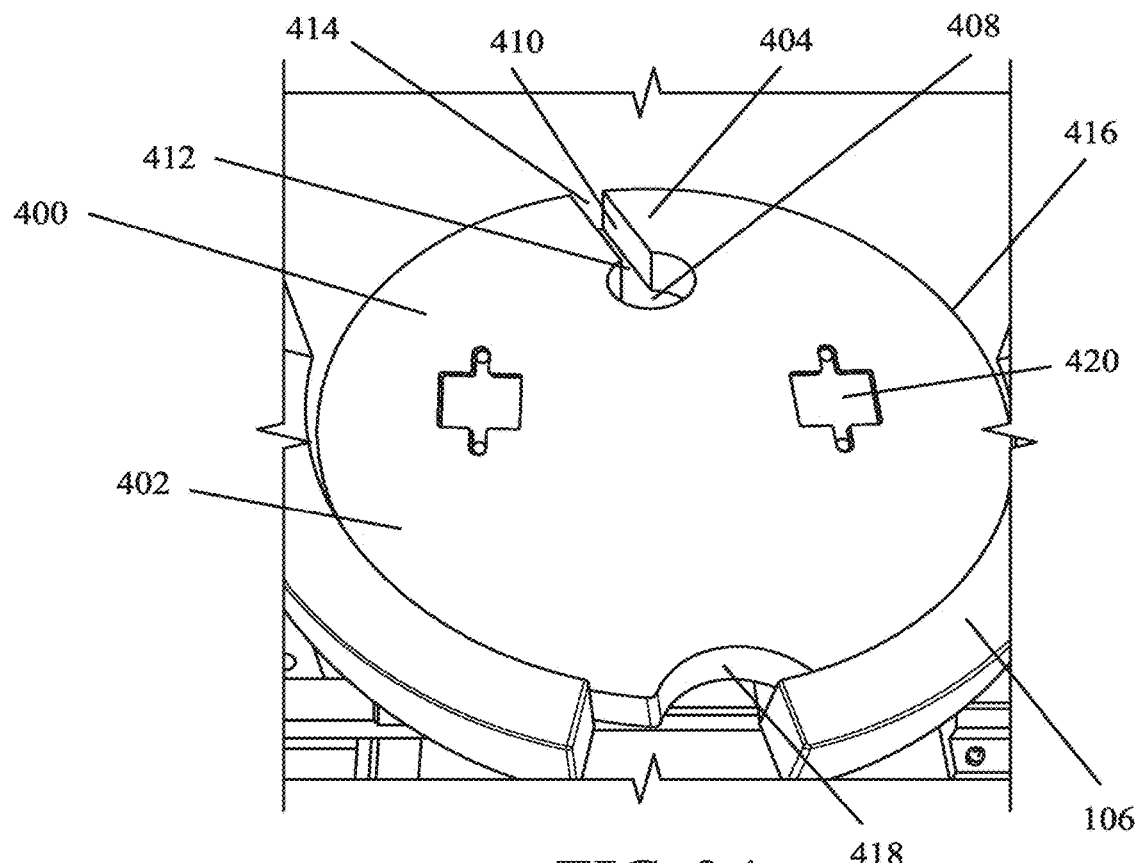
FIG. 3A-3B show top and side perspective views, respectively, of a bottom portion of a bioreactor described here, showing a spacer.
Figure 3B:
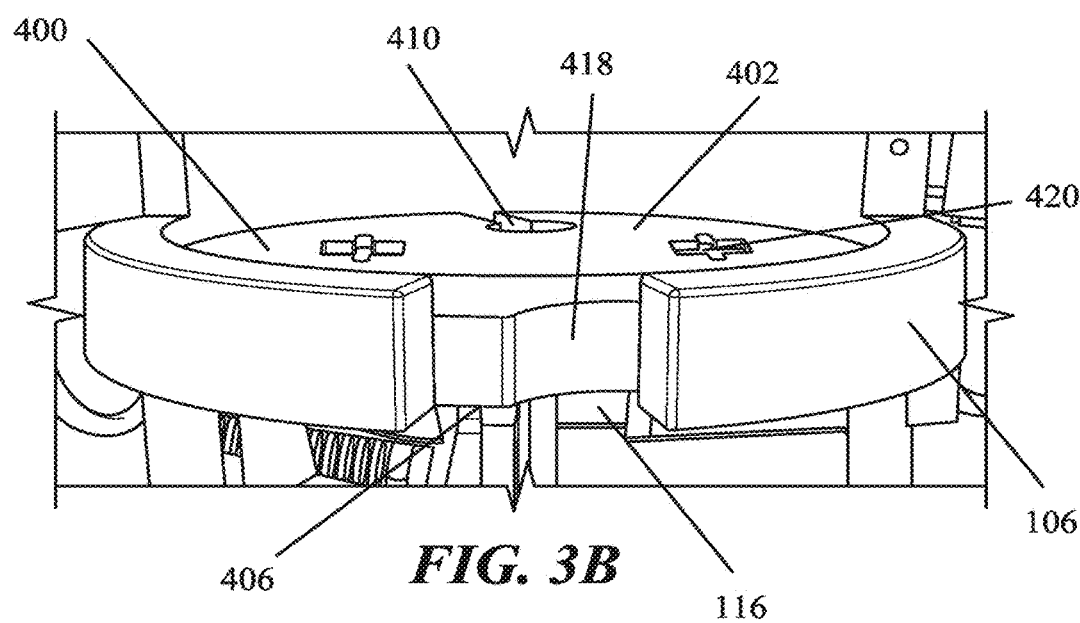

In some variations, the bioreactors described here may comprise a spacer 400 configured to fit near the bottom opening 116 or base 106 of the support structure 102. More specifically, the spacer 400 may rest on or be attached to the base 106 of the support structure 102, as shown in FIGS. 3A-3B. The spacer 400 may be configured to be placed in the support structure 102 when the bioreactor is used with a container configured for use with a top-mounted agitator motor (e.g., bag 214), while the spacer 400 may be removed from the support structure 102 when the bioreactor is used with a container configured for use with a bottom-mounted agitator motor (e.g., bag 208). When the spacer 400 is in the support structure, the top surface 402 of the spacer 400 may provide a raised support surface for the bottom of the container, create a smooth surface for the bottom of the container, and/or prevent the bottom of the container from contacting the bottom-mounted agitator motor 302 and/or any structures associated with the bottom-mounted agitator motor 302 (e.g., a protrusion) in variations of the bioreactor having a bottom-mounted agitator motor. For example, the bag 208 may have a conically-shaped bottom portion, while bag 214 may have a flat bottom portion, and thus, the spacer 400 may be placed in the support structure 102 when the bag 214 is used, in order to create a flat bottom for the bag 214, while the spacer 400 may be removed from the support structure 104 when the hag 208 is used, in order to accommodate the conically-shaped bottom portion of bag 208.

The spacer 400 may comprise any suitable material or materials. In some variations, the spacer 400 may comprise a material having low density, such that the spacer 400 may be more easily moved in and/or out of the support structure 102. For example, the spacer 400 may comprise a polymer, such as but not limited to polyoxymethylene or ultrahigh molecular weight polyethylene. The spacer 400 may be sized and shaped to fit within the support structure, and in some variations, may have the same cross-sectional (e.g., transverse to the longitudinal axis) shape as the support structure and/or base of the support structure. The spacer 400 may have any suitable thickness, such as but not limited to about 1 to 2 inches, about 2 to 4 inches, about 4 to 8 inches, or greater. In some variations, the spacer 400 may have a variable thickness.

In some variations, the spacer 400 may optionally comprise other features. For instance, the spacer 400 may comprise a slot 404 running from the top surface 402 to the bottom surface 406. In variations in which the spacer 400 is used with a container having tubing attached to the bottom of the container, the slot 404 may allow the tubing to pass through the spacer 400. As shown in FIG. 3A, in some variations the slot 404 may comprise a substantially circular region 408 and a substantially rectangular region 410, which may be connected at a first end 412 of the substantially rectangular region 410. A second end 414 of the substantially rectangular region 410 may extend to the outer edge 416 of the spacer 400. As another example, the spacer 400 may comprise an indentation 418 at the outer edge 416 of the spacer 400. Like the slot 404, the indentation 418 may allow for tubing exiting the container to pass through or around the spacer 400. In some variations, the indentation 418 may be located approximately radially opposite the slot 404. While shown in FIGS. 3A-3B as shaped as a portion of a cylinder, it should be appreciated that in other variations, the indentation 418 may have other suitable shapes. It should also be appreciated that in other variations, the spacer may have any configuration of slots, recesses, or openings that may be configured to allow tubing or other components to pass through or around the spacer, and the spacer need not have the specific configurations shown in FIGS. 3A-3B. In other variations, the spacer may not comprise any slots, recesses, or openings. The spacer 400 may additionally or alternatively comprise two depressions 420. These depressions allow a handle to be attached to the spacer, allowing it to be more easily removed from the support structure. It should be appreciated that the spacer may in other variations have other features to assist with its removal, such as tabs or attached handles, or in yet other variations, the spacer need not have any features to assist with its removal. Although the spacer 400 is described above with respect to bioreactor 100 having multiple agitator motors, it should be appreciated that the bioreactor 800 described herein having a single adjustable-position agitator motor may also comprise a spacer having similar design and features.

Figure 4A:
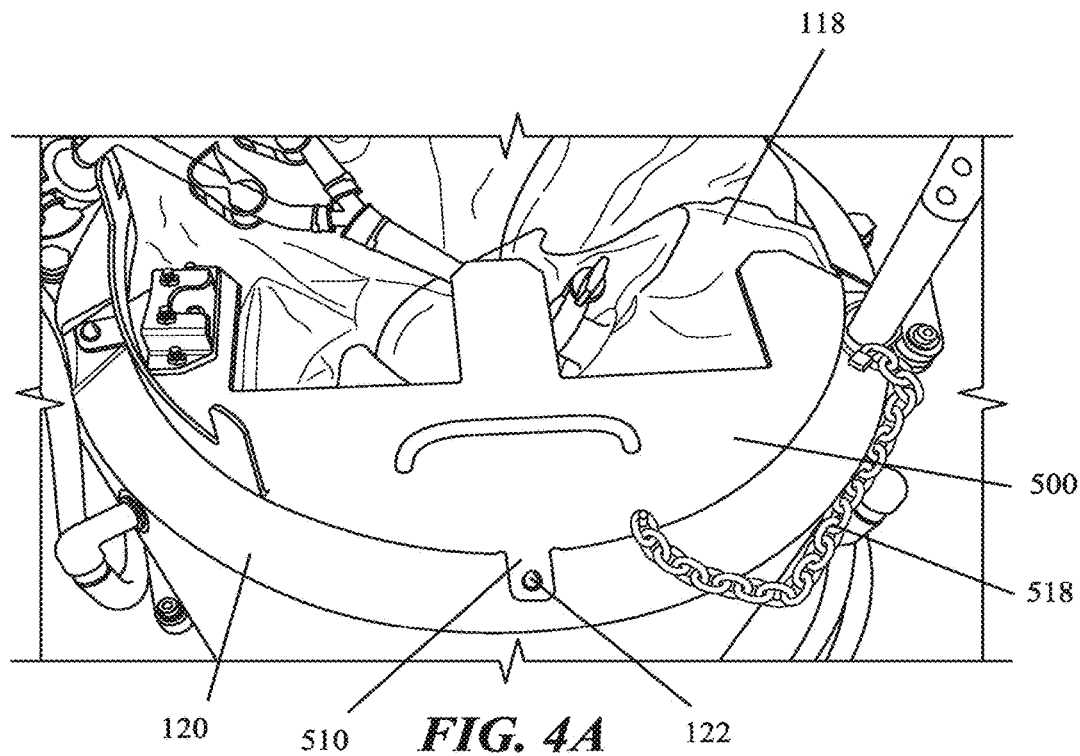
FIGS. 4A-4C show top portions of an embodiment of a bioreactor described here, showing a moveable lid.
Figure 4B:
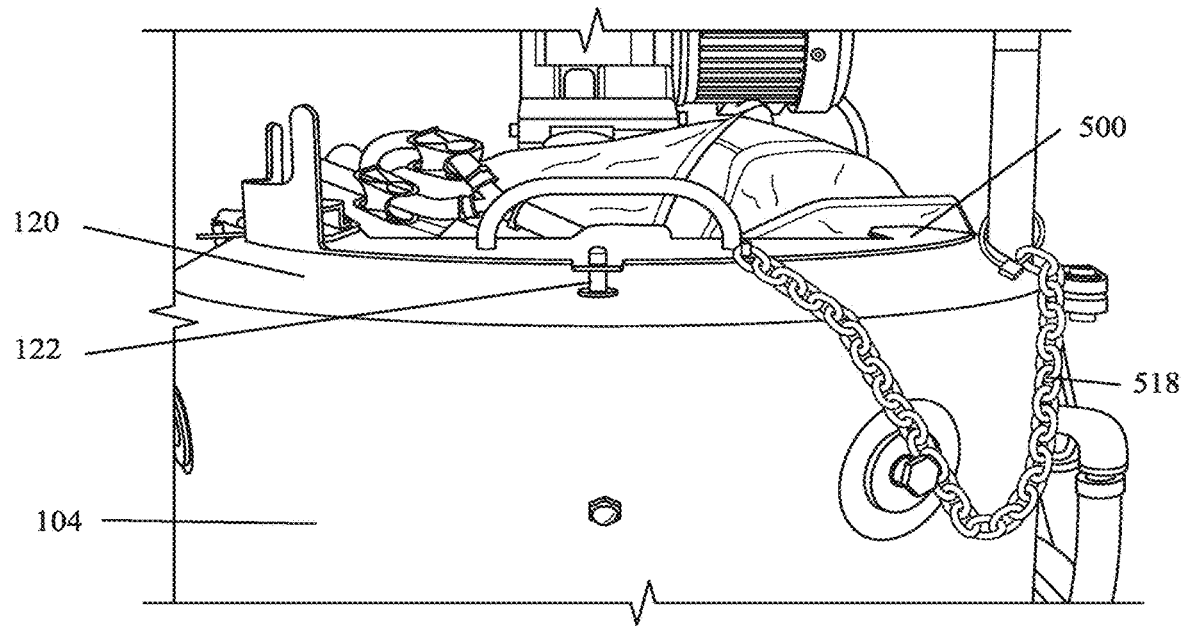
Figure 4C:
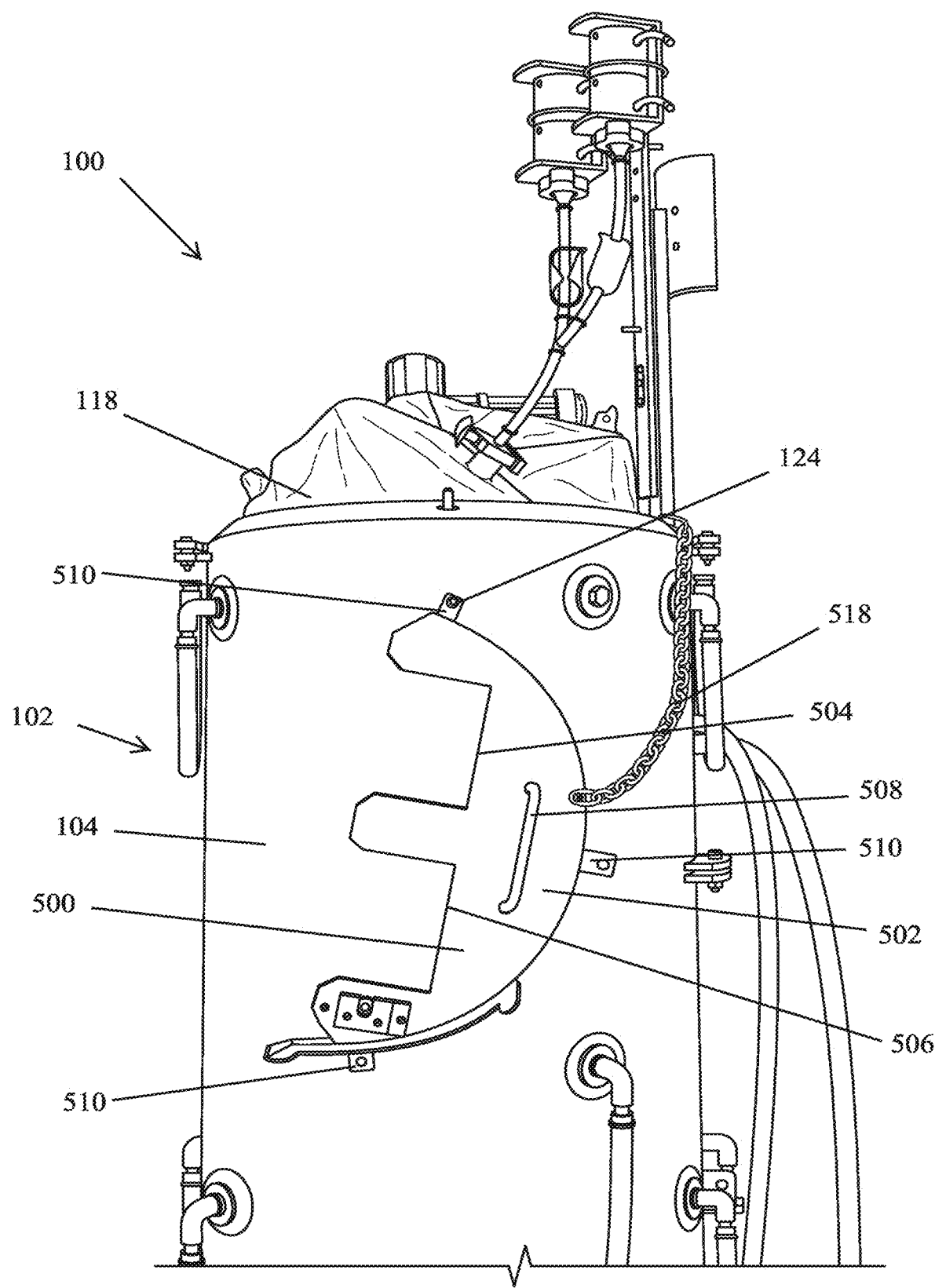

As shown in FIGS. 4A-4C, in some variations, the bioreactor 100 may comprise a lid 500. A lid may be desirable when a bioreactor described herein is used with a container configured for use with a bottom-mounted agitator motor (e.g., bag 208), for purposes such as but not limited to assisting with organization of tubing associated with the bioreactor and supporting one or more baffles. On the other hand, it may be desirable to have greater headspace near the top opening of the support structure when the bioreactor is used with a container configured for use with a top-mounted agitator motor (e.g., bag 214). The lid 500 may therefore be moveable between a first position and a second position, where the second position provides more headspace near the top opening of the support structure and/or increases internal access to the support structure. Thus, the lid 500 may generally be in the first position when the bioreactor is used with a container configured to be used with a bottom-mounted agitator motor (e.g., bag 208), while the lid 500 may generally be in the second position when the bioreactor is used with a container configured for use with a top-mounted agitator motor (e.g., bag 208).

In some variations as shown with respect to bioreactor 100, in the first position the lid 500 may be attached to or otherwise positioned near the top opening 118 of the sidewall 104, fully or partially covering the top opening 118. As shown in FIGS. 4A-4B, in the first position the lid 500 may be attached to the lip 120 of the sidewall 104. The attachment may be via one or more bolts or screws 122 extending from the lip 120, which may be configured to interface with one or more tabs 510 extending from the lid 500. The bolts or screws 122 and tabs 510 may allow the lid 500 to be fixed in the first position. While the variation shown in FIGS. 4A-4C comprises three bolts 122 and tabs 510, it should be appreciated that the lid 500 and the lip 120 may be connected at fewer or more (e.g., one, two, four, five, six, or more) points. It should also be appreciated that the lid 500 may be attached via another mechanism, such as by a clip or slot.

In the second position, the lid 500 may not cover the top opening 118 of the sidewall 104. In some variations, the lid 500 may be fully removable from the bioreactor 100, such that in the second position it is not attached to the bioreactor 100 and can be placed elsewhere. In other variations, such as the variation shown in FIG. 4C, when the lid 500 is in the second position it may be attached to some portion of the bioreactor 100, such that the lid 500 is not misplaced. For example, the lid 500 may be attached to a flexible element or tether 518 (e.g., a chain or cord), which may in turn be attached to another portion of the bioreactor 100 (e.g. lip 120 of sidewall 104), such that the tether 518 resists complete detachment of the lid 500 from the bioreactor 100. In some variations comprising a tether 518, the tether 518 may be configured such that the lid 500 can be in both the first position and the second position while the tether 518 remains attached to both the lid 500 and the other portion of the bioreactor 100. The lid 500 may additionally or alternatively be configured to be attached directly to some portion of the bioreactor 100. For example, the sidewall 104 of the support structure 102 may comprise a bolt 124 configured to interface with one of the tabs 510 on the lid 500.

The lid 500 may have any suitable shape. In some variations, the shape of the lid may be configured to assist in holding in place the container, any baffles, and/or tubing extending from the container. In the variation of FIGS. 4A-4C, the lid may comprise a circular segment 502 having two cut-out regions 504 and 506, which may be rectangular as shown. The lid 500 may optionally comprise a handle 508, which may facilitate movement of the lid 500. Although the lid 500 is described above with respect to bioreactor 100 having multiple agitator motors, it should be appreciated that the bioreactor 800 described herein having a single adjustable-position agitator motor may also comprise a lid having similar design and features.

Generally, bioreactors may comprise one or more inlet ports and one or more outlet ports that allow movement of components (e.g., fluids or gases) in and out of the container. The inlet ports may be coupled to tubing lines, for example, for delivering components such as media and cell cultures. The inlet ports may also comprise a sparger configured to deliver gases needed for the processes carried out within the bioreactor, such as but not limited to oxygen, carbon dioxide, nitrogen, and the like. The flow through these ports may be controlled by mass flow controllers. For example, in some variations, the bioreactors may comprise a set of mass flow controllers for air, oxygen, carbon dioxide, and nitrogen. These may have flow rates as required by the process to be carried out, such as about 20 slpm, about 20 slpm, about 5 slpm, and about 10 slpm, respectively. The outlet ports may comprise a sample line. Bioreactors may also generally comprise locations for one or more probes. The probes may be configured to measure temperature, pH, dissolved oxygen, dissolved carbon dioxide, pressure, mixing rate gas flow rate, and the like. Just as single-use bioreactors generally have support structures with agitator systems where the configuration of the support structure (e.g., having a top- or bottom-mounted agitator motor) generally restricts the use of containers to those configured for use with the support structure, single-use bioreactors similarly usually have port and probe configurations such that only certain containers can be effectively used with certain support structures.

Figure 5A:
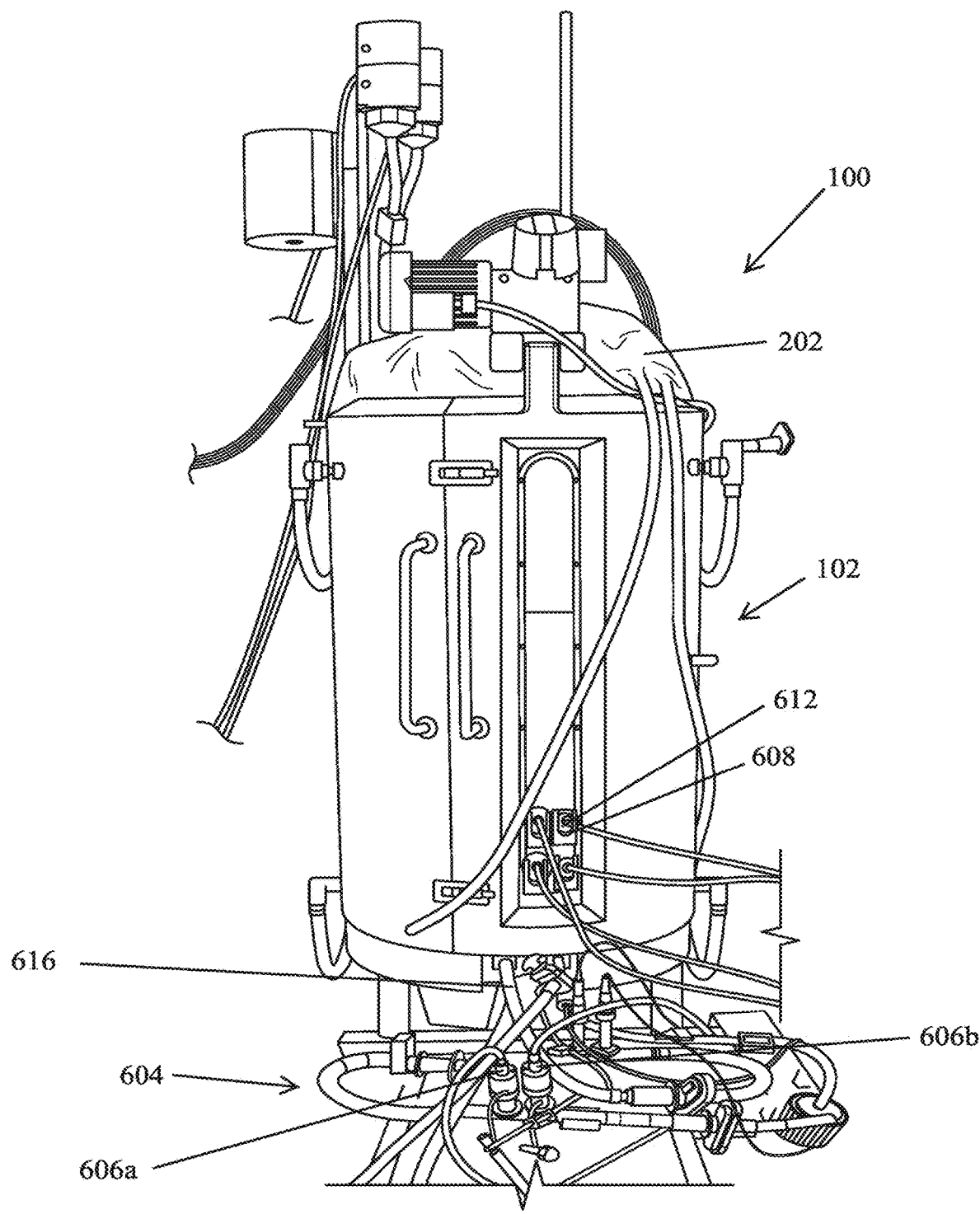
FIG. 5A illustrates a side perspective view of a bioreactor described here configured for use with a plurality of probe configurations.
Figure 5B:
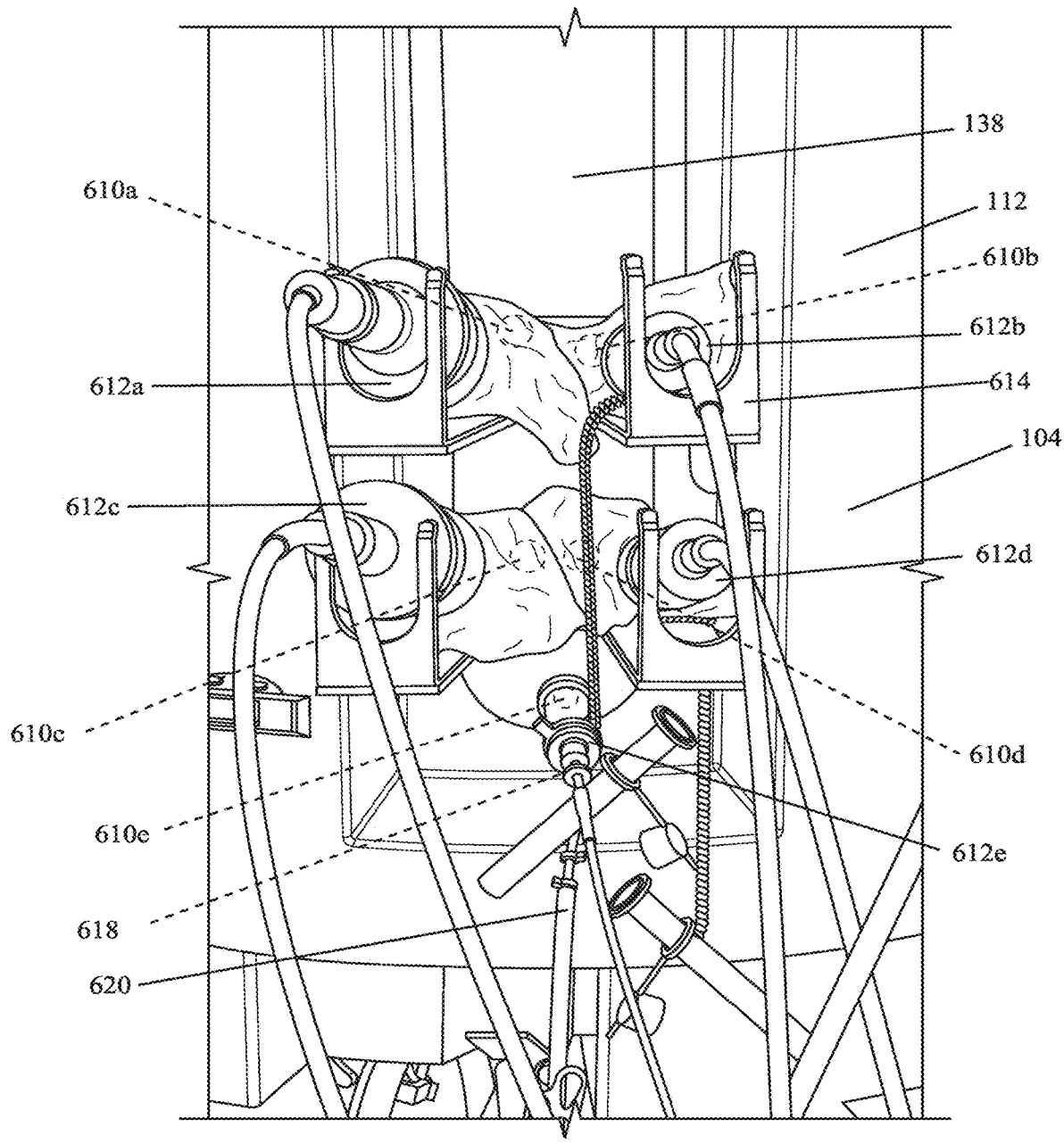
FIG. 5B is a close-up view of a lower portion of the bioreactor of FIG. 5A.

In contrast, the bioreactors described herein may comprise a plurality of configurations for ports and probes, such that more than one container design may be used with the support structure. In some variations, the bioreactors described here may be configured for use with containers having different configurations of inlet and outlet ports and spargers, and their accompanying tubing lines. For example, the spacer 400 described above may be placed in or removed from the support structure 102 as appropriate to accommodate tubing or a sparger at the bottom of the container; similarly, the lid 500 may be placed in first or second positions described above as appropriate to accommodate tubing at the top of the container. In some variations, the bioreactors described herein may be configured for use with containers configured for internal probes and for use with containers configured for external probes. For example, in the variation of FIGS. 5A-5B, the bioreactor 100 may comprise an external sensor loop 604 (shown in FIG. 5A) configured for use with external probes 606, in addition to ports 608 configured for use with internal probes 612. The external sensor loop 604 may be attached to the container 202 via tubing 616, and in some variations, may comprise an external pH probe 606a and an external dissolved oxygen probe 606b. Ports 608 configured for use with internal probes 612 may comprise openings 610 in the sidewall 104 of the support structure 102. In some variations, as shown in FIG. 5B, the openings 610 may be located on doors 112 (e.g., through window 138). Probe supports 614 may optionally be attached to the outside of the door 112 to support the internal probes 612 when inserted. In some variations, the openings 610 may comprise two top openings 610a and 610b configured for insertion of dual internal dissolved oxygen probes 612a and 612b, and two bottom openings 610c and 610d configured for insertion of dual pH probes 612c and 612d. The openings 610 may further comprise an opening 610e configured for insertion of temperature probe 612e. Door 112 may also comprise an opening 618 that may function as a sampling port via tubing 620. It should be appreciated that in other variations the openings may have different configurations and be configured for use with different types of probes, and that in some variations, such as variations of the bioreactor 100 not comprising doors, that the internal probes 612 may be configured to fit through other openings in the support structure 102, such as openings through the sidewall 104 or through openings in the base 106. It should also be appreciated that the support structure 102 may comprise more than one set of openings for internal probes (e.g., the support structure 102 may comprise two, three, four, or more different sets of openings), to allow the support structure 102 to be used with containers having more than one different internal probe port configuration.

Although the port and probe configurations are described above with respect to bioreactor 100 having multiple agitator motors, it should be appreciated that the bioreactor 800 described herein having a single adjustable-position agitator motor may also comprise similar port and probe configurations.

Bioreactors may also generally comprise one or more exhaust filters. The exhaust filters may be connected to the container via tubing and may allow for the venting of gas out of the container, which may prevent a build-up of pressure within the container. The exhaust filters are usually attached to or otherwise supported by the support structure of the bioreactor, and the bioreactor may generally comprise heating blankets that may prevent condensation within or plugging of the filters. The heating blankets are generally sized to fit particular exhaust filters, which may vary by container. As such, the heating blankets generally need to be compatible with the container used with the bioreactor support structure. Thus, like other features discussed above, the heating blanket design generally restricts the use of a support structure to use with compatible containers. However, it is desirable to be able to use the support structure with different containers, and thus it is desirable for bioreactors to comprise interchangeable or selectively employable heating blankets.

Figure 6:
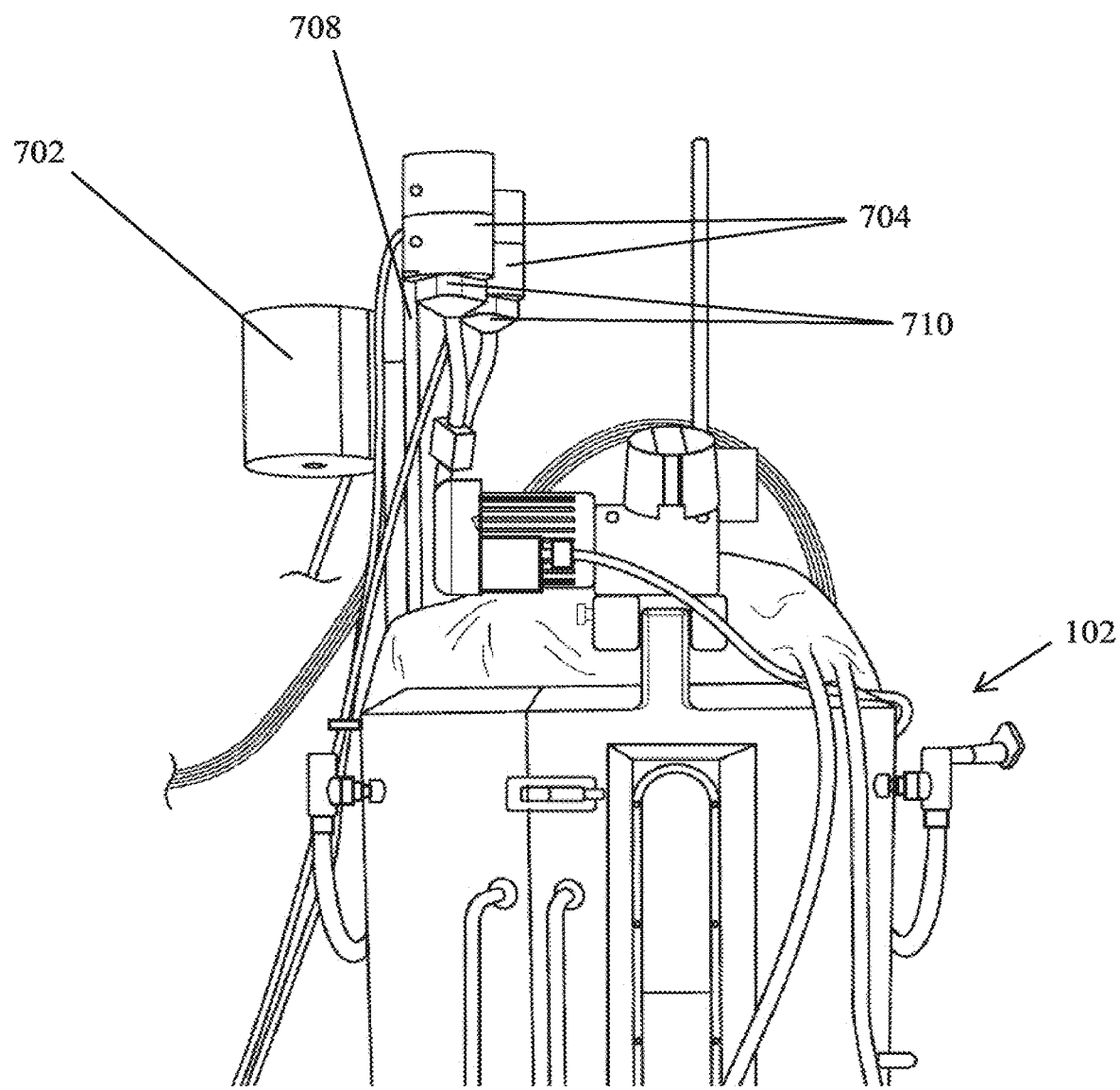
FIG. 6 depicts a perspective view of a top portion of an embodiment of a bioreactor described here having a plurality of selectively useable exhaust filter heating blankets.

As shown in FIG. 6, the bioreactor 100 may thus comprise at least one first heating blanket 702 having a first design and at least one second heating blanket 704 having a second design. The first heating blanket 702 and second heating blanket 704 may be configured for use with containers configured for use with different exhaust filter designs, and may be selectively employed based on the exhaust filter corresponding to the container configuration being used for a given process. For example, the heating blanket 702 and heating blanket 704 may have different sizes to accommodate differently sized exhaust filters. As shown in FIG. 6, there may be two (or more, e.g., three, four, or more) heating blankets 704. Additionally or alternatively, there may be two (or more, e.g., three, four, or more) heating blankets 702. It should be appreciated that in other variations, the bioreactor 100 may comprise more than two different designs of heating blankets (e.g., three, four, five, six, or more).

In some variations, the heating blanket(s) 702 and/or heating blanket(s) 704 may be mounted such that they can be physically moved. This may allow a heating blanket of a particular design to be moved closer to the container. As shown in FIG. 6, a rod 708 may extend vertically upward from the support structure 102. The heating blankets 702 and 704 may be attached to the rod 708. In some variations, the rod 708 may be rotatable about its longitudinal axis, such that the positions of the heating blankets 702 and 704 relative to the support structure 102 may be adjustable. For example, as shown in FIG. 6, the heating blankets 702 and 704 may be located on opposite sides of the rod 708, such that the rod 708 may be rotated by approximately 180 degrees in order to bring either the heating blanket(s) 702 or the heating blanket(s) 704 closer to the container. As shown, the rod 708 is rotated such that heating blankets 704 are closer to the container, such that exhaust filters 710 can be more easily mounted within heating blankets 704. In other variations, the heating blankets 702 and 704 may be spaced apart by less than approximately 180 degrees, and thus rod 708 may be rotated by an accordingly smaller angle in order to bring either the heating blankets 702 or 704 closer to the container. In yet other variations, the rod 708 may have an adjustable length instead of or in addition to being rotatable. In these variations, heating blankets 702 and 704 may be located at different vertical distances from the support structure 102 (either on the same side of rod 708, opposite sides of rod 708, or spaced apart by an intermediate radial distance), and the length of rod 708 may be adjusted to bring heating blankets 702 or 704 closer to the container. It should also be appreciated that in other variations, the heating blankets may be connected to the support structure via other mechanisms, or the heating blankets may be attached to an alternative structure rather than the support structure 102, such as a separate stand or cart. Although the heating blankets are described above with respect to bioreactor 100 having multiple agitator motors, it should be appreciated that the bioreactor 800 described herein having a single adjustable-position agitator motor may also comprise heating blanket configurations having similar design and features.

Also described herein are methods of modifying an existing support structure to be used with a container not originally configured to be used with the existing support structure. In some variations, this may comprise modifying an existing single-agitator motor support structure to be a multi-agitator motor support structure. For example, a support structure having the general configuration of support structure 102 described above, but having a single top- or bottom-mounted agitator motor, may be modified to add a second agitator motor, such that the modified support structure has both a top- and a bottom-mounted agitator motor. When the original support structure comprises a bottom-mounted agitator motor (like the bottom-mounted agitator motor 302 described above), the modification may be carried about by mounting a top-mounted agitator motor (like the top-mounted agitator motor 304 described above) near the top of the sidewalk in one of the configurations described above with respect to the mounting of the top-mounted agitator motor 304 of bioreactor 100. The modification may alternatively or additionally be carried out by mounting the top-mounted agitator in such a way as to allow it to be vertically adjustable, as described above with respect to top-mounted agitator motor 304 of bioreactor 100. In variations in which the top-mounted agitator motor is mounted to a door of the support structure, the door hinges may be reinforced to support the additional weight of the top-mounted agitator motor. In variations in which the top-mounted agitator motor is mounted to a portion of the sidewall containing a jacket for temperature regulation, the jacket may be modified to allow the mounting of the motor. Alternatively, when the original support structure comprises a top-mounted agitator motor, the modification may be carried out by mounting a bottom-mounted agitator motor near the bottom opening of the sidewall of the support structure. In some such methods comprising mounting a bottom-mounted agitator motor, all or a portion of a base of the support structure may need to be removed or otherwise modified. When a second agitator motor is added to the support structure, the method may further comprise adding a control system, like the control systems 306 and 308 described above, to the bioreactor, which may control the second agitator motor, as described above.

In other variations, the methods of modifying an existing support structure to be used with a container not originally configured to be used with the existing support structure may comprise modifying an existing single-agitator motor support structure having a fixed agitator motor to make the agitator motor have an adjustable position, having the features described above with respect to bioreactor 800. For example, the existing fixed agitator motor may be removed from the support structure and mounted in a way so as to be vertically, horizontally, radially, and/or rotationally adjustable, as described with respect to the adjustable agitator motor of the single-agitator bioreactor described above. In some such methods in which the existing single-agitator motor is a top-mounted agitator motor, all or a portion of a base of the support structure may need to be removed or otherwise modified to allow the agitator motor to be selectively positioned at a bottom position.

When the original support structure comprises a bottom-mounted agitator motor, the modification may further comprise adding a spacer, such as the spacer 400 described in detail above, near the bottom of the support structure. The spacer may provide support for a container configured for use with a top-mounted agitator motor, and/or create a smooth surface for such a container and prevent it from contacting the bottom-mounted agitator motor or associated structures, as described with respect to spacer 400 discussed in detail above.

When the original support structure comprises a bottom-mounted agitator motor, the modification may further comprise removing any existing lid on the support structure. This may provide more headspace near the top opening of the support structure, and/or may increase internal access to the support structure. In variations in which the original support structure comprises a lid that is integral to the sidewall of the support structure, the lid may be cut away from the sidewall to remove it. In some variations of the method, the lid may be further modified in order to allow the lid to be reattached to the support structure in a first position, and optionally, in a second position, where the first and second positions are as described above with respect to lid 500.

The method may additionally or alternatively comprise modifying the original inlet ports, outlet ports, and/or probe configurations to allow the support structure to be used with a container configured to be used with a bioreactor having different configurations of one or more of these elements. In some variations, this may comprise modifying the mass flow controllers or adding mass flow controllers to control the modified ports, for example to allow for higher mass flow rates. In variations in which the original support structure is configured to be used with an external sensor loop (like the external sensor loop 604 described above), the method may comprise creating ports in the support structure to accommodate internal probes, which may be done in one or more of the configurations described above with respect to ports 608 for internal probes 612 described above. The method may additionally or alternatively comprise adding one or more exhaust filter heating blankets to the bioreactor, which may be in one of the configurations described above with respect to exhaust filter heating blankets 702 and 704.

Also described herein are methods of manufacturing a multi-agitator motor or adjustable-position agitator motor bioreactor. In some embodiments, to manufacture such a bioreactor, a support structure comprising a sidewall configured to support, surround, and/or contain a container may be manufactured from any suitable material or materials, such as metals (e.g., stainless steel, aluminum, etc.), polymers (e.g., high-density polyethylene, polyacrylate, polycarbonate, polystyrene, nylon, or other polyamids, polyesters, phenolic polymers), glass, fiberglass, or the like. The support structure may have the features described in detail above with respect to support structure 102. In some variations, the method of manufacturing may comprise mounting a top-mounted agitator motor and a bottom-mounted agitator motor to the support structure. The top- and bottom-mounted agitator motors may be mounted to the support structure in any of the configurations described in detail above with respect to support structure 102, and the top- and bottom-mounted agitator motors may have the features described in detail above with respect to top-mounted agitator motor 304 and bottom-mounted agitator motor 302. The method of manufacturing may further comprise installing first and second control systems to control the bottom- and top-mounted agitator motors, respectively. The control systems may have the features described in detail above with respect to control systems 306 and 308. In other variations, the method of manufacturing may comprise attaching an adjustable-position agitator motor to the support structure in any of the configurations described above. In some variations, the method of manufacturing may comprise installing a temperature regulation system in the support structure. Installing a temperature regulation system may comprise installing electrical heating elements and/or circulating heated fluid systems, as described in more detail above with respect to the temperature regulation system of bioreactor 100.

The method of manufacturing may optionally comprise providing or manufacturing additional elements to go with the support structure, including but not limited to a support assembly and/or control cart, such as the support assembly 126 and control cart 144, described in more detail above. The method may also comprise creating one or more openings in the support structure to accommodate ports and probes, which may have one or more of the configurations described in detail above with respect to support structure 102. In some variations, the method of manufacturing may additionally or alternatively comprise mounting one or more exhaust filter heating blankets to the support structure. The exhaust filter heating blankets may have the features described in detail above with respect to heating blankets 702 and 704 and may be mounted in one of the configurations described in detail above.

In some variations, the method of manufacturing may comprise manufacturing a spacer configured to fit near the bottom opening of the support structure, and/or a lid configured to partially or fully cover the top opening of the support structure. The spacer may be manufactured from any suitable material, such as but not limited to a polymer such as polyoxymethylene or ultrahigh molecular weight polyethylene, and may have the features described in detail above with respect to spacer 400. The lid may also be manufactured from any suitable material, such as the material or materials used to manufacture the sidewall of the support structure, and may have the features described in detail above with respect to lid 500.

Also described herein are methods for operating the bioreactors described here, and the bioreactor support structures made as a result of the modification methods described here. The method may comprise first deciding whether to use a top- or bottom-mounted container, or deciding whether to use a top- or bottom-mounted agitator motor. This decision may be based on factors such as the particular process to be carried out for example, the production of certain products may be preferable in a bag of a certain material, which in turn may be available only in a top- or bottom-mounted configuration. As another example, the process may be preferably carried out using a bottom-mounted agitator motor due to the working volume during the process (and as a result, a bottom-mounted design may allow for pre-production and production in the same bioreactor, which may to cost savings or greater efficiency), or may be preferably carried out using either a top- or bottom-mounted agitator motor or particular bag design due to the mixing profile, sensitivity of cells or protein produced, or efficiency gains.

Thus, the method may comprise selecting a container for use with a support structure (e.g., support structure 102) of the bioreactor. The container may be a top-mounted container (e.g., bag 214 described in detail above) or a bottom-mounted container (e.g., bag 208 described in detail above). When the support structure has a multi-agitator motor design, a user may then select between a top-mounted agitator motor and a bottom-mounted agitator motor of the support structure based on the configuration of the selected container. Alternatively, when the support structure has an adjustable-position, single agitator motor design, the user may adjust the position of the agitator motor to the appropriate position. In other variations of the method, the method may comprise first selecting between a top-mounted agitator motor and a bottom-mounted agitator motor of the support structure, or selecting a position of an adjustable-position agitator motor, and then selecting between a top-mounted container and a bottom-mounted container based on the agitator motor or position selected.

The user may then determine whether a spacer (e.g., the spacer 400 described above) present within the support structure. If the container selected is a top-mounted container, the user may either confirm that the spacer is present within the support structure, or place the spacer inside the support structure (if the spacer is not present within the support structure). If the container selected is a bottom-mounted container, the user may either confirm that the spacer is not present within the support structure, or remove the spacer from the support structure (if the spacer is present within the support structure).

The container may then be placed into the support structure. In variations in which the support structure comprises one or more doors (e.g., doors 112), the one or more doors may be opened to facilitate placement of the container. In variations in which the container comprises one or more connectors and/or the support structure comprises one or more connectors, the container may be connected to the support structure via the connector(s). In some variations, the container may be fully or partially inflated before being placed into the support structure. This may decrease folding of the container during installation in the support structure in variations in which the container is a flexible bag. The container may be coupled to the selected agitator motor. In variations comprising an agitator port, the agitator port may be coupled to the agitator motor. In variations in which the agitator motor has an adjustable position, the vertical position of the agitator motor may be changed. For example, if a top-mounted container is selected that has a shorter height than the support structure, an adjustable-position top-mounted agitator motor may be moved downward, or an adjustable-position agitator motor may be moved to the appropriate position. In variations in which the impeller is mounted on an adjustable-length shaft, the vertical position of the impeller may be changed. For example, if a top-mounted container is selected and is intended to be used with a low working volume, the impeller may be moved downward.

The inlet and/or outlet ports of the container, as described in more detail above with respect to bioreactor 100, may be connected to the appropriate tubing lines. One or more probes may also be connected to the bioreactor. If the selected container is configured to be used with an external sensor loop (e.g., external sensor loop 604), the external sensor loop may be connected to the container. If the selected container is configured to be used with internal probes, the probes may be inserted through probe ports. In variations of the support structure having probe ports located in the sidewall of the support structure (e.g., on the doors in variations of the support structure having doors), the probes may be inserted through the sidewall of the support structure. In variations of the support structure having probe supports, the external probes may be placed in the probe supports to hold them in place. The appropriate exhaust filter(s) may also be attached to the container via tubing and placed in the heating blanket(s). In variations of the bioreactor in which the exhaust filter heating blankets are mounted such that they can be physically moved relative to the container (e.g., by being mounted on a rotatable rod such as rod 708), the position of the appropriate heating blanket(s) may be adjusted to bring the exhaust filter(s) closer to the container.

The user may further determine whether a removable lid (e.g., the lid 500 described above) is fully or partially covering a top opening of the support structure. If the container selected is a bottom-mounted container, the user may either confirm that the lid is partially or fully covering the top opening of the support structure, or place the lid over the top opening of the support structure (if the lid is not partially or fully covering the top opening of the support structure). If the container selected is a top-mounted container, the user may either confirm that the lid is not covering the top opening of the support structure, or remove the lid from the top opening of the support structure (if the lid is partially or fully covering the top opening of the support structure). In variations of the support structure where the lid remains attached to the support structure when removed from the top opening, if the user removes the lid, the user may then optionally attach the lid to a different portion of the support structure (e.g., the outside of sidewall in variations having a bolt or other element for holding the lid to the outside of sidewall).

Once the container is fully in place within the support structure and appropriately connected, the bioreactor can be used for the desired process. In doing so, the appropriate control system may be used to turn the agitator motor on or off, to control the rotation speed of the impeller, and/or to control the temperature of any heating blankets for the exhaust filters. In variations having a manual control switch for one or both of the agitator motors in a multi-agitator design, the manual control switch(es) may be used to select the appropriate agitator motor. In variations having a user interface (e.g., a digital user interface), the user interface may be used to control the selected motor.

What is claimed is:

1. A bioreactor, comprising:
   a support structure comprising a sidewall and a base, forming a cavity therein, the cavity configured to hold container designs, including:
      a first container design comprising an agitator motor interface only at a top portion of the container, and
      a second container design comprising an agitator motor interface only at a bottom portion of the container;
   a top-mounted agitator motor coupled to the support structure; and
   a bottom-mounted agitator motor coupled to the support structure;
   wherein a container having the first container design is configured to be used with the top-mounted agitator motor by attaching an impeller to an agitator shaft within the container having the first container design, and attaching the agitator shaft to the agitator motor interface at the top portion of the container such that the top-mounted agitator motor is configured to rotate the impeller within the container, and
   a container having the second container design is configured to be used with the bottom-mounted agitator motor by attaching the impeller to the agitator shaft within the container having the second container design, and attaching the agitator shaft to the agitator motor interface at the bottom portion of the container such that the bottom-mounted agitator motor is configured to rotate the impeller within the container.

2. The bioreactor of claim 1, further comprising at least one connector in at least one of the sidewall and base, configured to attach the container.

3. The bioreactor of claim 1, further comprising a container configured to reside in the cavity and to be coupled to the top- or bottom-mounted agitator motor, wherein the container is a collapsible bag.

4. The bioreactor of any one of claim 1, further comprising a spacer with a raised support surface configured to be removably positioned at the bottom of the support structure.

5. The bioreactor of claim 4, wherein the spacer is configured to separate the container and the bottom-mounted agitator motor when the spacer is at the bottom of the support structure.

6. The bioreactor of claim 1, further comprising a first control system configured to control the top-mounted agitator motor and a second control system configured to control the bottom-mounted agitator motor.

7. The bioreactor of claim 6, further comprising a selector to switch between the first and second control systems.

8. The bioreactor of claim 6, wherein the first and second control systems are configured to be selectively employed using a digital user interface.

9. The bioreactor of claim 6, wherein the first and second control systems comprise variable frequency drives.

10. The bioreactor of claim 1, wherein the support structure comprises a top opening and a removable lid configured to at least partially cover the top opening.

11. The bioreactor of claim 10, wherein the lid is attached to the support structure when covering the top opening and when removed from the top opening.

12. The bioreactor of claim 1, further comprising at least two exhaust filter heating blankets.

13. The bioreactor of claim 12, wherein the at least two exhaust filter heating blankets have different sizes.

14. The bioreactor of claim 12, wherein the at least two exhaust filter heating blankets are configured to be selectively employed based on the configuration of the container.

15. The bioreactor of claim 14, wherein the at least two exhaust filter heating blankets are mounted to a rotatable element, and wherein the at least two exhaust filter heating blankets are configured to be selectively employed by rotating the rotatable element.

16. The bioreactor of claim 1, wherein the support structure further comprises one or more probe access ports.

17. The bioreactor of claim 16, wherein at least one of the probe access ports is configured to accommodate an internal probe.

18. The bioreactor of claim 16, wherein the sidewall comprises a main body and a door, wherein the one or more probe access ports are located on the door of the sidewall.

19. The bioreactor of claim 1, wherein the sidewall comprises a main body and a door, and wherein the top-mounted agitator motor is mounted to the door.

20. The bioreactor of claim 1, wherein the sidewall comprises a main body and a door, and wherein the top-mounted agitator motor is mounted to the main body.

\* \* \* \* \*